US008875865B2

(12) United States Patent
Terzini

(10) Patent No.: US 8,875,865 B2
(45) Date of Patent: Nov. 4, 2014

(54) LINEAR DISPENSING SYSTEM WITH UNIVERSAL ESCAPEMENT

(75) Inventor: Robert Terzini, Corinth, TX (US)

(73) Assignee: Tension International, Inc., Kansas City, MO (US)

( * ) Notice: Subject to any disclaimer, the term of this patent is extended or adjusted under 35 U.S.C. 154(b) by 100 days.

(21) Appl. No.: 13/415,668

(22) Filed: Mar. 8, 2012

(65) Prior Publication Data

US 2012/0228083 A1   Sep. 13, 2012

Related U.S. Application Data

(60) Provisional application No. 61/451,008, filed on Mar. 9, 2011, provisional application No. 61/534,805, filed on Sep. 14, 2011.

(51) Int. Cl.
| | |
|---|---|
| *B65G 15/64* | (2006.01) |
| *G07F 11/62* | (2006.01) |
| *G07F 11/70* | (2006.01) |
| *G07F 17/00* | (2006.01) |

(52) U.S. Cl.
CPC ............ *G07F 11/70* (2013.01); *G07F 17/0092* (2013.01); *G07F 11/62* (2013.01)
USPC .................................. 198/345.1; 198/370.06

(58) Field of Classification Search
CPC ....................................................... B65G 47/24
USPC ............ 198/370.06, 345.1; 414/268; 221/92, 221/123, 131, 133
See application file for complete search history.

(56) References Cited

U.S. PATENT DOCUMENTS

| | | | |
|---|---|---|---|
| 3,067,891 A | 12/1962 | Anderson | |
| 3,624,792 A | 11/1971 | Lipfert | |
| 3,831,197 A | 8/1974 | Beach et al. | |
| 4,119,482 A | 10/1978 | Bennett | |
| 4,633,148 A | 12/1986 | Prucher | |
| 4,915,566 A * | 4/1990 | van Elten | ...................... 414/276 |
| 5,251,741 A | 10/1993 | Morishita et al. | |

(Continued)

FOREIGN PATENT DOCUMENTS

| | | | | |
|---|---|---|---|---|
| WO | WO 2012090079 | * | 12/2010 | ............. B65G 21/20 |

OTHER PUBLICATIONS

Wedge Stabilizer Mechanism for Sliding Console, IP.Com No. IPCOM000051652D; Publication date: Feb. 10, 2005.*

*Primary Examiner* — Ramya Burgess
*Assistant Examiner* — Lester Rushin
(74) *Attorney, Agent, or Firm* — Polsinelli PC; Marcia J. Rodgers; Derek D. Donahoe

(57) ABSTRACT

A linear dispensing system is provided that includes a plurality of channels, a pair of parallel rails, a plurality of carriers and a plurality of linear motor modules. The channels are configured to hold inventory products at an orientation. The pair of parallel rails is disposed at a bottom portion of the channels. The carriers are slidably disposed on the rails and have a conveyor unit configured to pick the inventory product from the channels while substantially maintaining the same geometric orientation as in the channel. The linear motor modules are disposed between the parallel rails and aligned end to end. The linear motor modules are coupled with the carriers and configured to pass the carriers to an adjacent linear motor module. Each carrier delivers a plurality of selected products of varying shapes to a universal escapement structure where the products are labeled, imaged, verified and dispensed.

37 Claims, 28 Drawing Sheets

(56) References Cited

U.S. PATENT DOCUMENTS

| | | | |
|---|---|---|---|
| 5,306,375 A * | 4/1994 | Leonard | 156/249 |
| 5,380,139 A | 1/1995 | Pohjonen et al. | |
| 5,417,537 A | 5/1995 | Miller | |
| 5,427,492 A | 6/1995 | Tanaka et al. | |
| 5,468,110 A | 11/1995 | McDonald et al. | |
| 5,755,335 A * | 5/1998 | Michelotti et al. | 209/528 |
| 5,988,352 A * | 11/1999 | Ballestrazzi et al. | 198/405 |
| 6,029,851 A | 2/2000 | Jenkins et al. | |
| 6,038,490 A | 3/2000 | Dimitri et al. | |
| 6,208,908 B1 | 3/2001 | Boyd et al. | |
| 6,464,142 B1 | 10/2002 | Denenberg et al. | |
| 6,490,502 B2 | 12/2002 | Fellows et al. | |
| 6,522,945 B2 * | 2/2003 | Sleep et al. | 700/225 |
| 6,874,684 B1 | 4/2005 | Denenberg et al. | |
| 6,876,896 B1 * | 4/2005 | Ortiz et al. | 700/112 |
| 6,983,579 B2 | 1/2006 | Rice et al. | |
| 7,006,893 B2 | 2/2006 | Hart et al. | |
| 7,016,043 B2 * | 3/2006 | Fukumori et al. | 356/432 |
| 7,093,755 B2 | 8/2006 | Jordan et al. | |
| 7,228,198 B2 | 6/2007 | Vollm et al. | |
| RE39,747 E | 7/2007 | Peltier et al. | |
| 7,410,098 B2 | 8/2008 | Denenberg et al. | |
| 7,537,155 B2 | 5/2009 | Denenberg et al. | |
| 7,866,506 B2 | 1/2011 | Daniels et al. | |
| 7,970,490 B2 | 6/2011 | Fellows et al. | |
| 8,028,822 B2 | 10/2011 | Braunstein | |
| 8,231,749 B2 | 7/2012 | Dent et al. | |
| 8,380,535 B2 | 2/2013 | Denenberg et al. | |
| 8,392,020 B2 | 3/2013 | Terzini | |
| 8,726,617 B2 | 5/2014 | Gustafsson | |
| 2003/0089731 A1 | 5/2003 | Mayer et al. | |
| 2003/0111321 A1 * | 6/2003 | Van Oss et al. | 198/426 |
| 2009/0050267 A1 | 2/2009 | Conlon et al. | |
| 2010/0059585 A1 | 3/2010 | Fellows et al. | |
| 2010/0176145 A1 | 7/2010 | Hawkes et al. | |
| 2011/0056172 A1 * | 3/2011 | Klenk et al. | 53/268 |
| 2011/0146213 A1 | 6/2011 | Terzini | |
| 2011/0146835 A1 | 6/2011 | Terzini | |
| 2014/0017044 A1 * | 1/2014 | Hawkes et al. | 414/268 |

* cited by examiner

LINEAR DISPENSING SYSTEM WITH UNIVERSAL ESCAPEMENT

CROSS-REFERENCE TO RELATED APPLICATIONS

This application claims priority under 35 U.S.C. 119(e) and 37 C.F.R. 1.78(a)(4) based upon U.S. Provisional Application Ser. No. 61/451,008 for LINEAR DISPENSING SYSTEM filed Mar. 9, 2011, which is incorporated herein in its entirety by reference and U.S. Provisional Application Ser. No. 61/534,805 for LINEAR DISPENSING SYSTEM WITH UNIVERSAL ESCAPEMENT filed Sep. 14, 2011, which is incorporated herein in its entirety by reference.

TECHNICAL FIELD

The present invention generally relates to a product dispensing system. More specifically, the invention relates to an automated linear dispensing system for stored products having various shapes.

BACKGROUND INFORMATION

Material handling systems enable businesses that maintain an inventory of stored products to distribute products from the inventory based on customer orders. Automated distribution of stored products requires product verification in order to avoid distribution of the wrong product, or failure to distribute a product at all. In some industries, such as pharmaceutical distribution and the like, individual product labeling may also be required prior to distribution. The stored product inventory may include products of many types, sizes and shapes which may be maintained in storage at a warehouse facility, or at a retail outlet or other location. Pharmacies, for example, such as high volume mail order/central-fill, specialty, and acute and long-term care facility-based pharmacies, dispense a wide variety of stored products from inventory to large numbers of patients. The pharmaceutical products are stored at an inventory location, where a pharmacist or technician individually selects products from the inventory for dispensing. Pharmaceutical product dispensing includes labeling the selected product with the patient's information and dosing instructions or usage directions, as well as verifying the accuracy of the labeled product.

The prior art describes various attempts to automate the above-described process by providing automated systems for pulling numerous products from inventory and then transporting the products away from the inventory for dispensing. Some of the prior art automated systems rely on elaborate mechanisms to pull the product from inventory. The automated systems often utilize a vehicle on a conveyor to carry the mechanism, along with the product, away from the inventory for labeling. An example of a conveyor frequently used is an endless conveyor. The vehicles on an endless conveyor move in direct relation to the other vehicles. That is, the vehicles do not have independent coordinated movement. Therefore, any given vehicle is dependent upon the movement of the conveyor as well as the other vehicles when it pulls products from the inventory. This dependent movement inhibits the ability of the system to pull different products from different inventory locations and especially limits the ability to simultaneously pull products from more than one inventory location. This dependent movement also decreases efficiency and increases the amount of space necessary for operation of the system.

The automated systems in the prior art also add unnecessary steps and machinery between the steps of obtaining the product and labeling it. In particular, after delivering the product to the conveyor, the conveyor transports the product toward a labeler which must orient the product using sensors to ensure that the label is applied correctly. In other words, previous automated systems obtain and transport the product without regard to an orientation needed to correctly apply the label, thereby necessitating an extra step in the process to reorient the product before application of a label.

Prior art systems select only identically shaped products for transport to a labeler. Product sensors at the labeler station are designed to handle and verify only products of the selected shape. Separate labeling and verification stations equipped with shape-specific equipment must therefore be provided for flat and round or irregularly shaped products.

Accordingly, there exists a need for an improved inventory product distribution, verification and labeling system that uses independent, coordinated carriers or dependent carriers for efficient movement in less space, that can maintain the products in a preselected orientation so as to enable labeling of the products without the need for reorientation, and that can select, transport, label and verify the products without regard to shape. This disclosure addresses this need in the art as well as other needs, which will become apparent from the disclosure.

SUMMARY

A linear dispensing system includes a plurality of channels, a pair of parallel rails, a plurality of carriers and a plurality of linear motor modules. The channels are configured to maintain the inventory products at a preselected orientation. A pair of parallel rails is disposed at a bottom portion of the channels. Carriers are slidably disposed on the rails and include a conveyor unit configured to pick the inventory product from the channels while substantially maintaining the same orientation of the product as in the channel. Linear motor modules are disposed between the parallel rails and may be aligned end to end. The linear motor modules are connected to the carriers and configured to pass the carriers to an adjacent linear motor module.

In one embodiment, the linear dispensing system also includes a labeler module and a discharge guide assembly. The linear track assembly includes one or more motor units, rails and one or more carriers slidably engaged with the rails. The linear motor module is disposed on the rails and has a motor to move the carrier. The carrier communicates with the motor unit and has a conveyor unit configured to pick the inventory product from the channels and substantially maintain the same orientation as in the channel. The labeler module is configured to label the inventory products in substantially the same orientation. The discharge guide assembly forms a chute for receiving the inventory product from the carrier and directs the inventory product to the labeler module at substantially the same orientation.

In another embodiment, the linear dispensing system includes a product carrier having a plurality of product receiving zones capable of receiving products of diverse shapes and a universal escapement connected to the linear dispenser for receiving, labeling and performing multi-step verification of the products at a single station without regard to the shape of the product.

In another embodiment, the universal escapement may be a freestanding unit, unconnected to the linear dispenser and it may be manually loaded. In still other embodiments, the escapement may be integrated with other existing devices.

These and other objects, features, aspects and advantages of the present disclosure will become apparent to those skilled in the art from the following detailed description, which, taken in conjunction with the annexed drawings, discloses a preferred embodiment of the present invention.

BRIEF DESCRIPTION OF DRAWINGS

Referring now to the attached drawings which form a part of this original disclosure.

DETAILED DESCRIPTION

Selected embodiments of the present disclosure will now be explained with reference to the drawings. It will be apparent to those skilled in the art from this disclosure that the following descriptions of the embodiments are provided for illustration only and not for the purpose of limiting the invention as defined by the appended claims and their equivalents.

Figure 1:
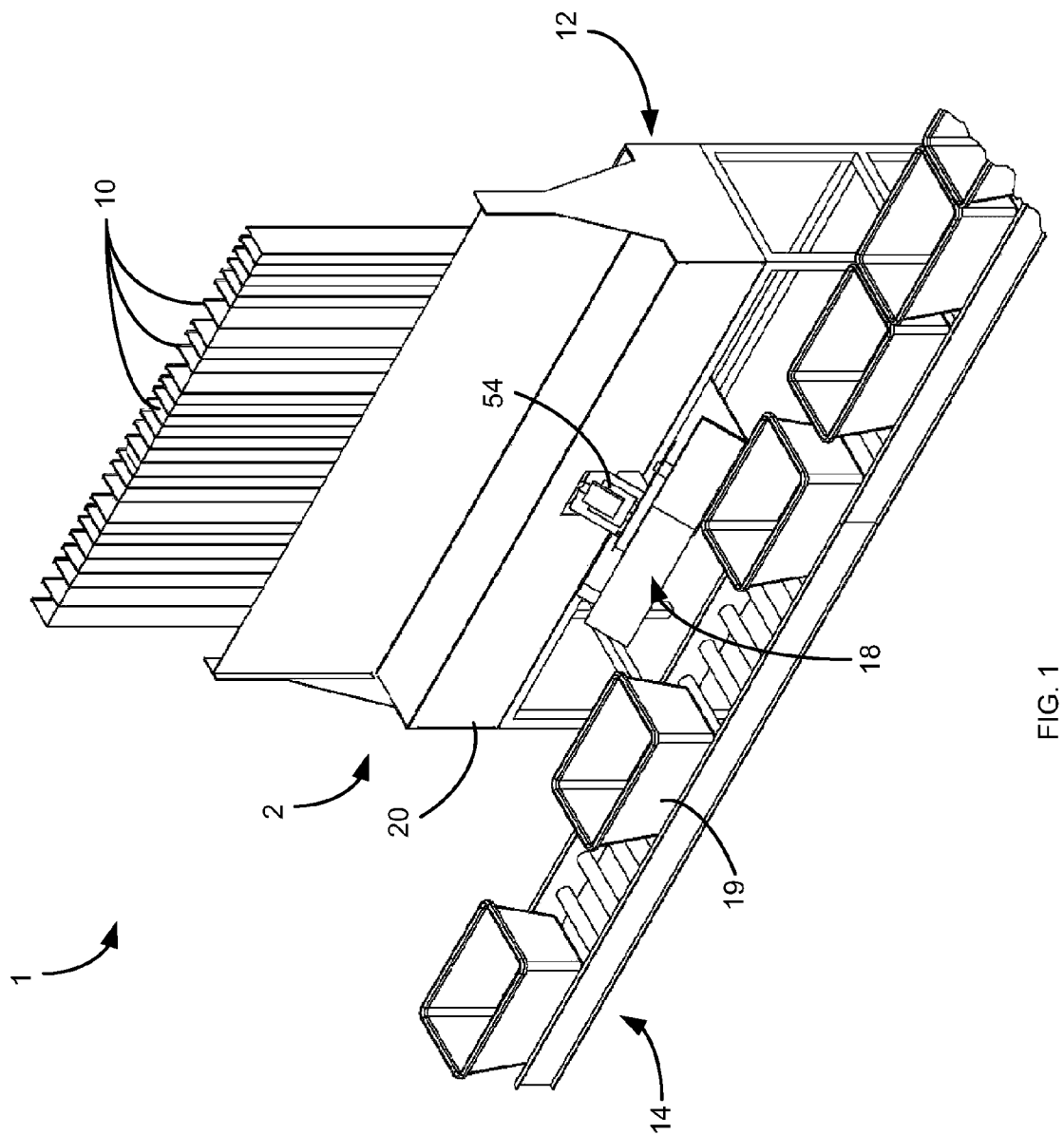
FIG. 1 is a front perspective view of a linear dispensing system.

Referring initially to FIG. 1, a linear dispensing system 1 is illustrated in accordance with a first embodiment of the present disclosure. The linear dispensing system 1 is advantageous in that it can pick different inventory products varying in size and shape from storage either individually or simultaneously. The linear dispensing system 1 also provides efficient handling of the inventory products from storage to dispensing and labeling. Once a product is picked from the stored inventory, the linear dispensing system 1 maintains the product at the same or substantially the same angular or three dimensional orientation in space.

Figure 1A:
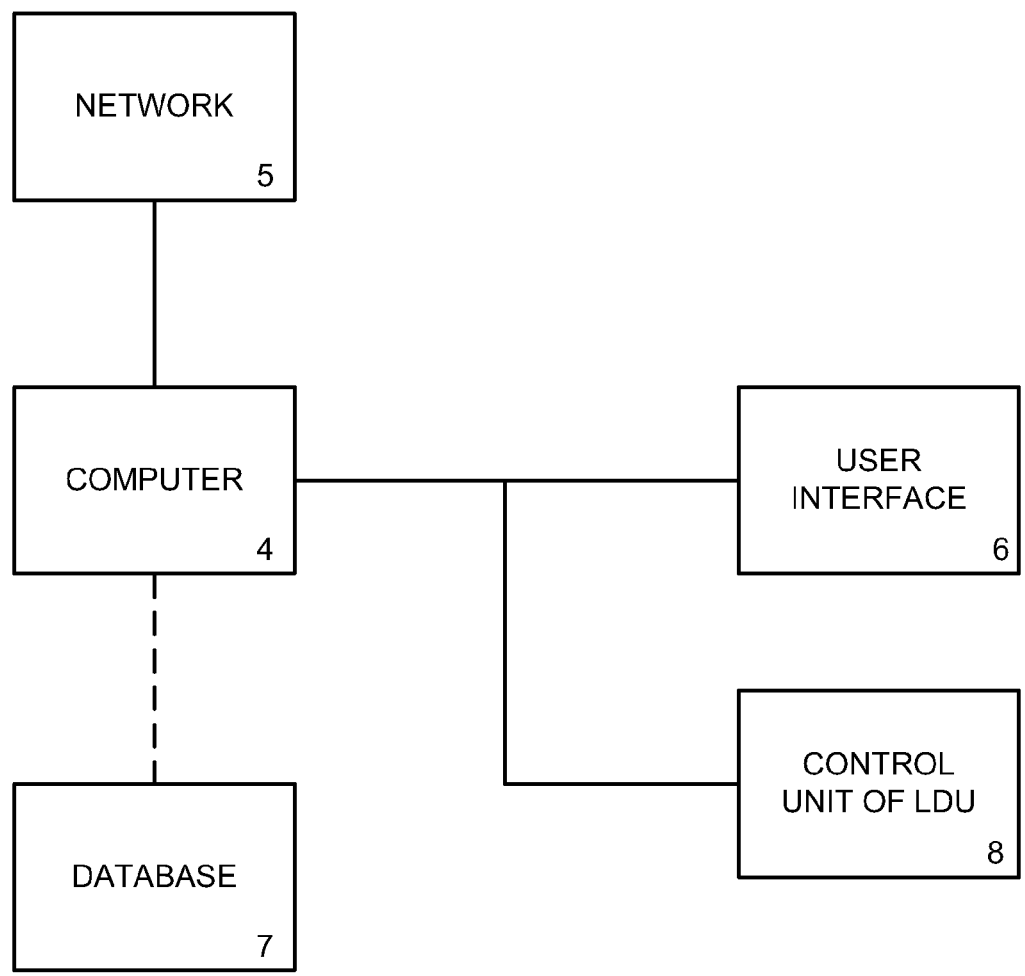
FIG. 1A is a diagram of a control system of the linear dispensing system.
Figure 2:
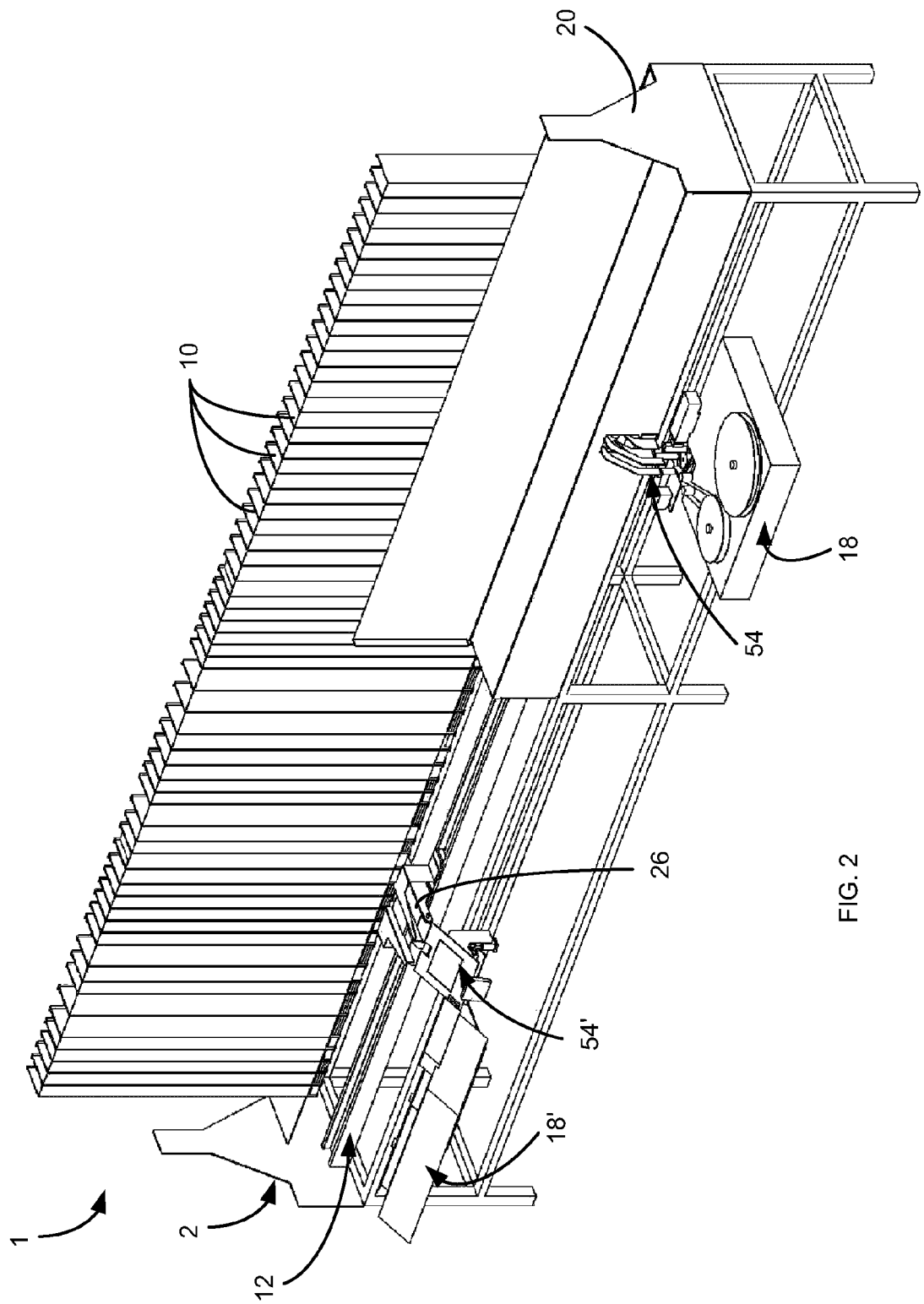
FIG. 2 is a front perspective view of an embodiment of the linear dispensing system including dual escapement features.

As shown in FIG. 1 and FIG. 1A, the linear dispensing system 1 includes a linear dispensing unit 2 and a control unit 8 in communication with a computer 4 and/or a user-interface 6. Although not shown in FIG. 1, control unit 8 is in electrical communication with the linear dispensing unit 2, either through wired or wireless communication. The linear dispensing unit 2 stores inventory products of many different types and shapes for picking, dispensing and labeling, as needed. The user interface 6 is preferably a hand-held device in wired or wireless communication with the control unit 8 of the linear dispensing system 1. The user-interface 6 provides an interface for the user to control the operation of the linear dispensing unit 2 by, for example, entering parameters or commands for processing by the control unit 8. For example, the user may enter or input parameters related to the inventory in response to receiving information, such as an alert for a low level of inventory, and to input parameters or commands for processing by the control unit 8. The control unit 8 uses a programmable logic controller or other control system to process communications and control operations of components in the linear dispensing unit 2.

In one embodiment, a computer 4 or other personal computing device may be used in place of or in conjunction with the user interface 6 to communicate with the control unit 8. Computer 4 (as well as user interface 6 and control unit 8) may include one or more processors for executing one or more computer-readable programs. To facilitate operation, the components may also include a memory controller for interfacing a main memory with the one or more processors for retrieving information, such as instructions of a program, and/or storing information used by the system. The system may also include an input/output (I/O) interface to interface I/O devices with the processors. I/O devices may also include an input device (not shown), such as an alphanumeric input device, including alphanumeric and other keys for communicating information and/or command selections to the processors. Another type of user input device includes cursor control, such as a mouse, a trackball, or cursor direction keys for communicating direction information and command selections to the processors and for controlling cursor movement on the display device.

Computer 4 may include a dynamic storage device, referred to as main memory, or a random access memory (RAM) or other computer-readable devices for storing information and instructions to be executed by the processors. Main memory also may be used for storing temporary variables or other intermediate information during execution of instructions by the processors. In addition, the computer 4 may be connected to a network 5 through one or more network communication ports to provide information or receive information to the network. In one embodiment, the network is the Internet and the network communication port includes an Internet modem. As described in more detail below, the computer 4 may receive information, such as information concerning a product associated with the linear dispensing system 1, which may be used by the system during retrieval of one or more products. Alternatively, or in conjunction with the network 5, the computer 4 may be in communication with one or more databases 7 to store information concerning the linear dispensing system 2.

Figure 3:
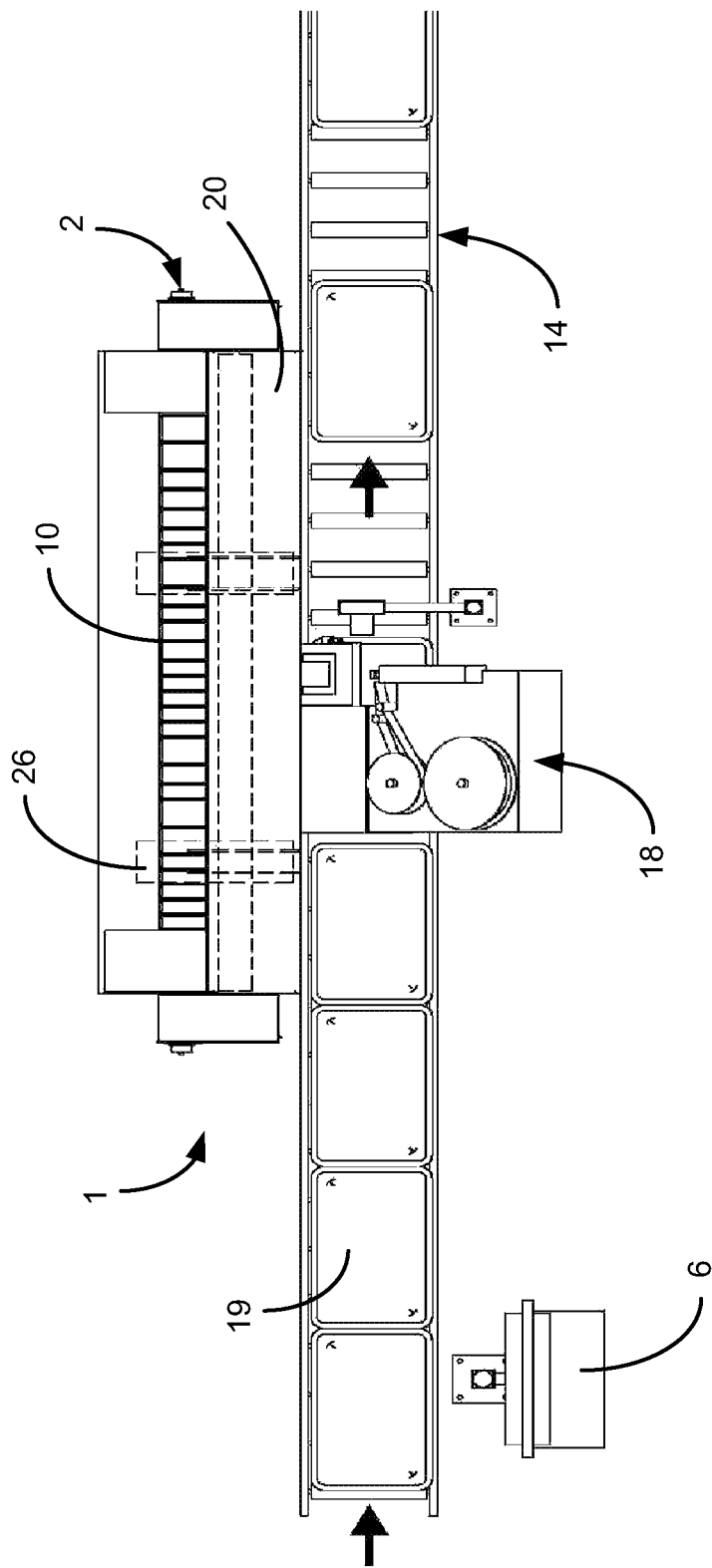
FIG. 3 is a schematic representation of the linear dispensing system.
Figure 3A:
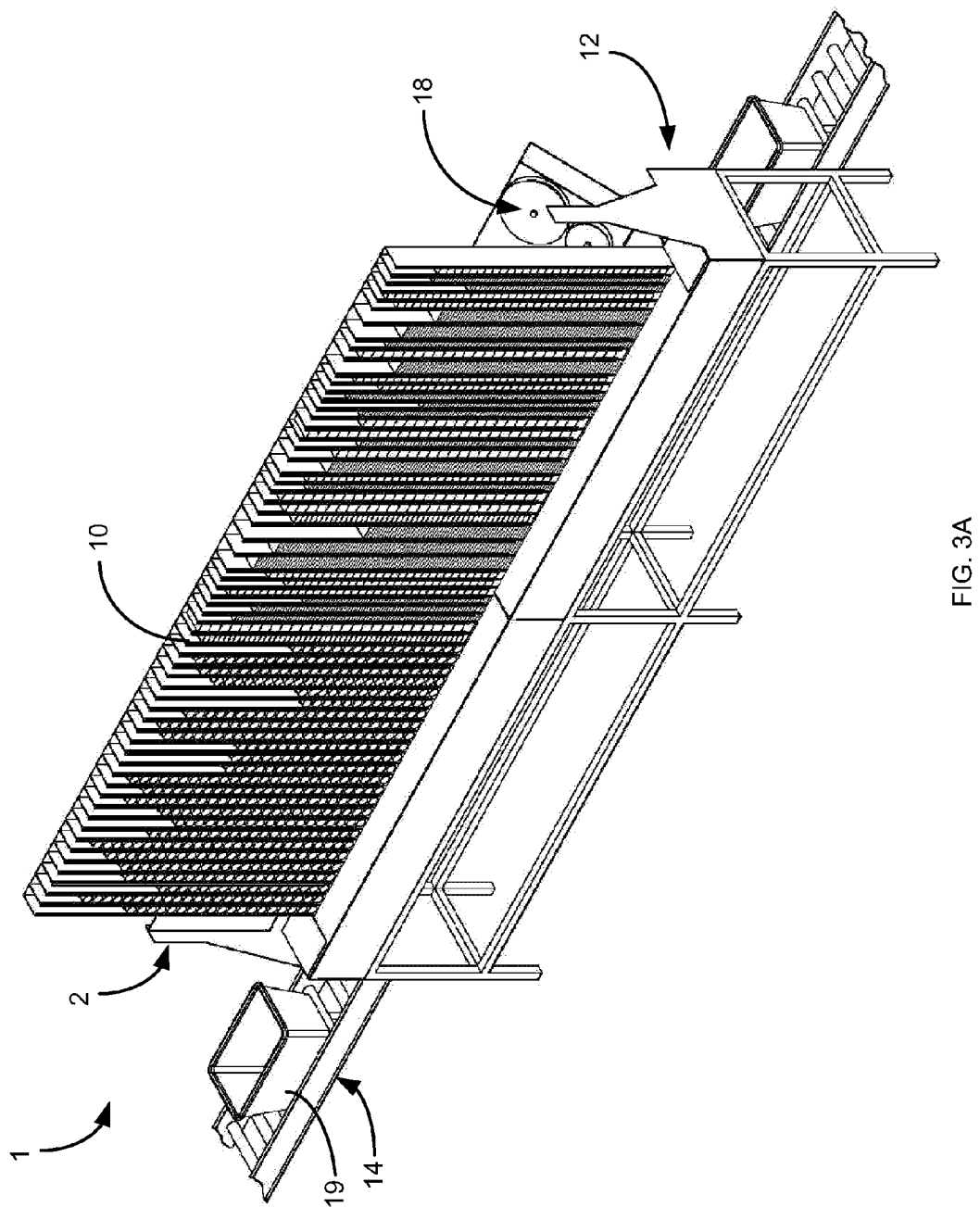
FIG. 3A is a rear perspective view of the linear dispensing system.

Referring now to FIGS. 1-3A, the linear dispensing unit 2 of the first embodiment includes a plurality of channels 10, a linear track assembly 12, a receiving track or conveyor assembly 14 and one or more labeler modules 18, 18'. The channels 10 are disposed parallel to one another in a row and extend outwardly from the linear track assembly 12. The channels 10 preferably extend outwardly at an incline of from about 3° to about 50°, for example, to maintain the inventory products in a nested relation and to limit escape from the channel 10. An end or bottom portion of each of the channels 10 is connected to the linear track assembly 12 to enable automated access to the inventory products held by the channels 10. In one embodiment, the channels 10 are categorized into cylindrical and non-cylindrical holding areas. However, in other embodiments, the cylindrical and non-cylindrical channels may be intermingled or not categorized into specific areas. The channels 10 have walls that form both cylindrical and non-cylindrical holding areas. The walls are movable for sizing each of the channels 10 in accordance with the size and shape of the inventory product it will hold. Referring to FIG. 3A, it can be seen that various channels 10 are sized to hold cylindrical inventory products, while other channels are sized to hold non-cylindrical inventory products. Although shown in FIG. 3A as having the cylindrical and non-cylindrical inventory products disposed at respective ends of the linear dispensing unit 2, the cylindrical and non-cylindrical channels may be intermingled. Further, in one embodiment, the size or width of each channel 10 is set by an operator of the system 1 during population of the channel with product. In another embodiment, the width of the channel may be set automatically by the system 1 upon receipt at the control unit 8 of data regarding the type and size of product intended for a particular channel. In either case, the channel 10 walls are spaced to accommodate products of varying shapes and sizes.

Figure 3B:
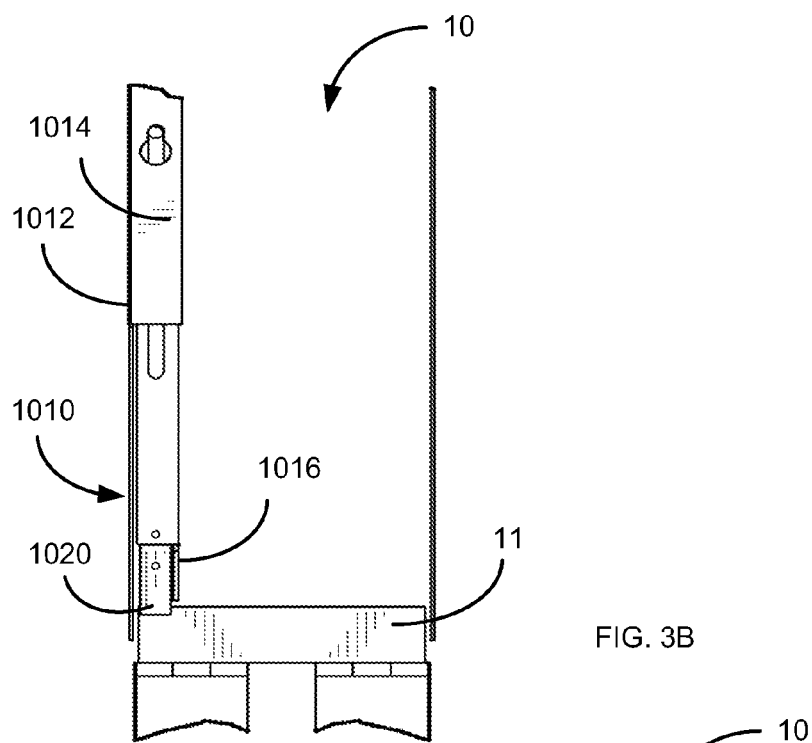
FIG. 3B is a front elevational view of an exit portion of a channel of the linear dispensing system.
Figure 3C:
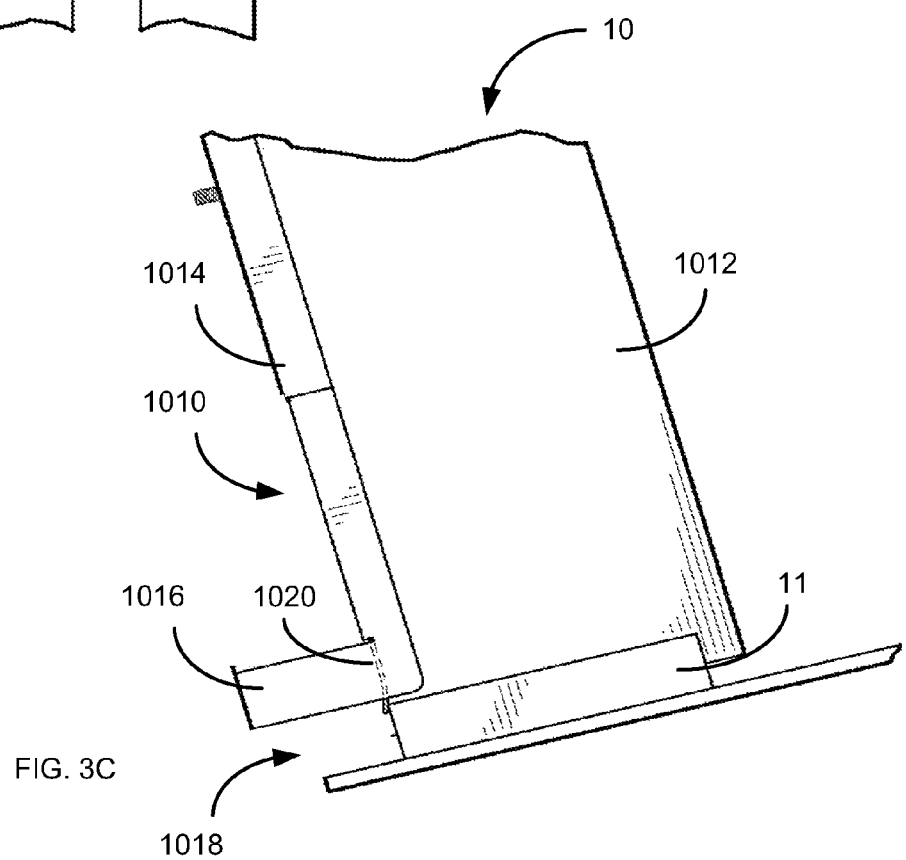
FIG. 3C is a side elevational view of the exit portion of the channel.

The channels 10 may be formed to accommodate and hold the various-shaped products. As such, in addition to the sidewalls, the channels 10 may include a front wall or front retaining structures 1010 to maintain the products within the channel. In one embodiment, shown in FIGS. 3B and 3C the front retaining structure 1010 is generally "L"-shaped and is oriented in the channel 10 to maintain the product 11 in the channel. In the embodiment shown, the L-shaped retainer 1010 abuts a sidewall 1012 of the channel 10. In another embodiment, however, the L-shaped retainer 1010 may be positioned away from the sidewall 1012, such as in the channel 10. The L-shaped retainer 1010 generally includes a vertical portion 1014 that abuts the stacked products 11 in the channel 10 and a horizontal portion 1016 at or near the bottom of the retainer. The L-shaped retainer 1010 may be mounted in the channel 10 to provide a retrieval opening 1018 at that bottom of the channel such that the product 11 may be pulled through the retrieval opening during operation of the unit 2. As such, the retrieval opening 1018 may be at least the same height as the product 11 stored in the channel 10 to allow passage of the product through the opening. In some embodiments, the height of the retrieval opening 1018 is adjustable to accommodate different sized products.

A retaining spring 1020 is mounted on the vertical portion 1014 of the L-shaped retainer 1010 and extends below the retainer at least partially into the retrieval opening 1018. In the embodiment shown in FIGS. 3B and 3C, the retaining spring 1020 is a flexible rectangular piece of metal or plastic that includes sufficient tensile strength to retain the product 11 within the channel 10. However, during retrieval of the product 11, the retaining spring 1020 may bend to allow the product to pass below the retaining spring and through the retrieval opening 1018. Additionally, the horizontal portion 1016 of the L-shaped retainer 1010 may prevent the product 11 from pitching vertically during retrieval of the product through the retrieval opening 1018. Upon removal of the bottom-most product 11 from the channel 10, the remaining products in the channel are oriented to slide down the channel such that another product is in position against the retaining spring 1020 for later retrieval by the unit 2.

Returning to FIGS. 1-3A, the linear dispensing unit 2 further includes a housing 20 to cover the linear track assembly 12 for protection against misalignment, for example, by dirt or foreign objects and the like and to prevent injury to an operator of the system. In one embodiment, the housing 20 may include one or more access panels that include a hinge such that the panels may be opened to allow access to the linear track assembly for maintenance. Such access panels may also include one or more safety switches that detect when an access panel is open and remove power to the system 2. A receiving track assembly 14 is disposed at a location below the linear dispensing unit 2 to facilitate receipt of the inventory items after they have been retrieved and labeled by the labeler module 18. The receiving track assembly 14 includes a plurality of totes 19 (FIG. 1) movably disposed thereon to receive the labeled inventory products. The totes 19 move along the receiving track assembly 14 to facilitate delivery of numerous labeled inventory products.

The present linear dispensing system advantageously maintains the inventory product in a preselected angular or spatial orientation to permit uniform labeling during retrieval of the product. That is, the linear dispensing unit 2 is configured to maintain the spatial orientation of the inventory product from the point where it is picked from the channel 10 to the time it is released to the receiving track assembly 14. This is allows for barcode reading for product verification such that many different types of uniform labeling systems may be integrated with the linear dispensing unit 2. For example, this enables the same label to be applied to both large and small items, and to flat or rounded items. It also enables a large or long label, such as a patient information package insert, to be folded into a "flag" and glued or otherwise attached to a bottle, box, tube or other container that is smaller than the label.

Referring to the embodiment of FIGS. 6-8A and 18A-18C, the linear track assembly 12 includes a track 22, having parallel rails 24, one or more carriers 26, 26A-26C and a plurality of linear motor modules 28, 28A-28C. The carriers 26 are movably disposed on the track 22, between the parallel rails 24, and above the linear motor modules 28, which are aligned end-to-end between the parallel rails 24. The carriers 26 are configured to slide or roll along the track 22 to predetermined positions in front of one or more of the channels 10. In one embodiment, the carriers 26 include wheels for travel along the rails 24.

Each linear motor module 28 includes a linear actuator, such as a linear induction motor, linear synchronous motor, linear timing belt and stepper motor, linear electric actuator or a pneumatic rodless actuator. While these and other suitable linear actuators may be utilized, the linear synchronous motor is preferred because it provides the ability to pass carriers 26 from one module 28 to another, as described in more detail below. A carrier 26 actuated by another type of linear actuator, such as a pneumatic rodless actuator, cannot be passed from one actuator to another and therefore, its movement is limited by the length of the linear actuator. In the illustrated embodiment utilizing a linear synchronous motor, position sensing is accomplished through a motor stator winding of the linear motor module 28, so there is little or no reliance on external position sensors. It will be apparent to one of ordinary skill in the art from this disclosure, however, that position sensors can be included in the linear track assembly 12 and connected to the control unit 8 if additional feedback is desired.

Referring to FIGS. 5-8, each of the carriers 26 includes a frame 30, a guide mechanism 32, a permanent magnet 33 and a conveyor unit 35. The linear synchronous motor of the linear motor module 28 uses a modular long stator design which permits the linear motor modules 28 to link together to create an actuator along any desired length of track 22. The linear motor module 28 creates an electromagnetic force to propel the carrier 26 in a desired direction by moving the permanent magnet 33 to a predetermined position along the track 22.

The frame 30 extends between the parallel rails 24 and provides underlying support for the carrier 26. The guide mechanism 32, permanent magnet 33 and conveyor unit 35 are disposed on the frame 30. The guide mechanism 32 maintains the same (or substantially the same) orientation of the product as the product is moved from one of the channels 10 to the labeler module 18. The guide mechanism 32 cooperates with the conveyor unit 35 to guide the inventory product from the channel 10 and direct it along the conveyor unit 35 toward the inner surface of the housing 20. The conveyor unit 35 is a dynamic unit that obtains the inventory product and moves it into position for discharge while maintaining the product in the same geometric orientation that the inventory product had when it was disposed in the channel 10.

The guide mechanism 32 includes a first guide member 34, a second guide member 36, a first guide support 38, a second guide support 40 and a guide actuator (not shown). The first and second guide members 34, 36 are disposed at an upper surface of the conveyor unit 35 to guide the inventory product as it moves along the conveyor unit 35. The first and second guide members 34, 36 are generally parallel to one another and extend longitudinally across the conveyor unit 35. The first and second guide supports 38, 40 are movable supports that link the respective first and second guide members 34, 36 to the guide actuator 42. The first and second guide supports 38, 40 extend upwardly from the frame 30 of the carrier 26 and inwardly to support the first and second guide members 34, 36 at the conveyor unit 35. The guide actuator preferably includes a stepper motor to achieve accurate, fine intervals of movement of the guide supports 38, 40 and the guide members 34, 36. The guide actuator spaces the first and second guide members 34, 36 apart to substantially match an outer dimension of the inventory product by opening and closing the first and second guide members 34, 36 to substantially match a width of the preselected channel 10, thereby maintaining the inventory product in the same orientation as it leaves the channel 10. In this embodiment, the guide actuator moves each of the first and second guide members 34, 36 toward or away from its compliment in intervals of equal distance. The control unit 8 commands movement of the guide actuator according to the selected channel's 10 width, which is stored in a non-volatile memory of the control unit 8.

In one embodiment, a guide member position sensor (not shown) is located on the frame 30 to detect the location of the guide members 34, 36. More particularly, the guide member position sensor provides a notification signal to the control unit 8 that the guide members 34, 36 are in a "home" or preset position. To space apart the guide members 34, 36, the control unit 8 activates the guide actuator to move the guide members to the home position before moving the guide members to the desired spacing. As explained in more detail below, the desired spacing may be obtained by the control unit 8 from the user interface 6 or computer 4 and is based on information stored in memory of the control unit or obtained by the computer from the database 7 and/or network 5.

Figure 7:
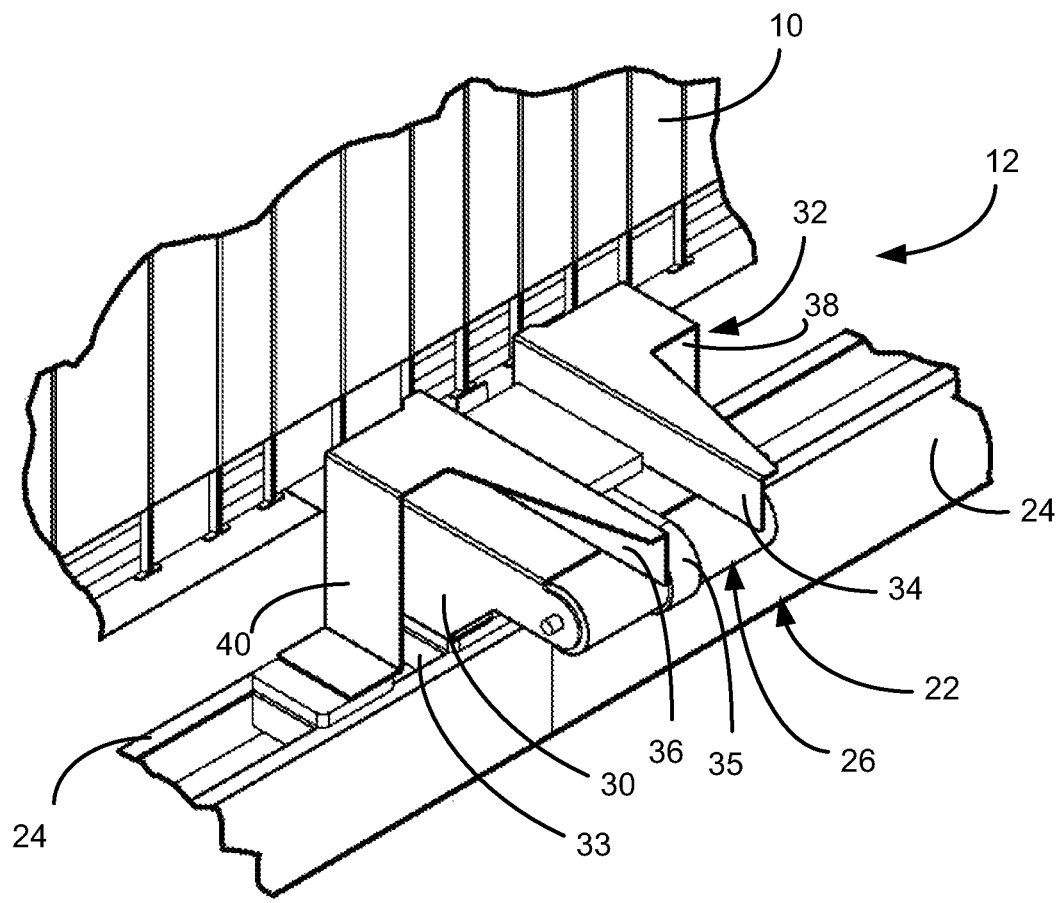
FIG. 7 is a perspective view of a carrier of the linear dispensing system guiding a non-cylindrical inventory product.
Figures 8, 8A:
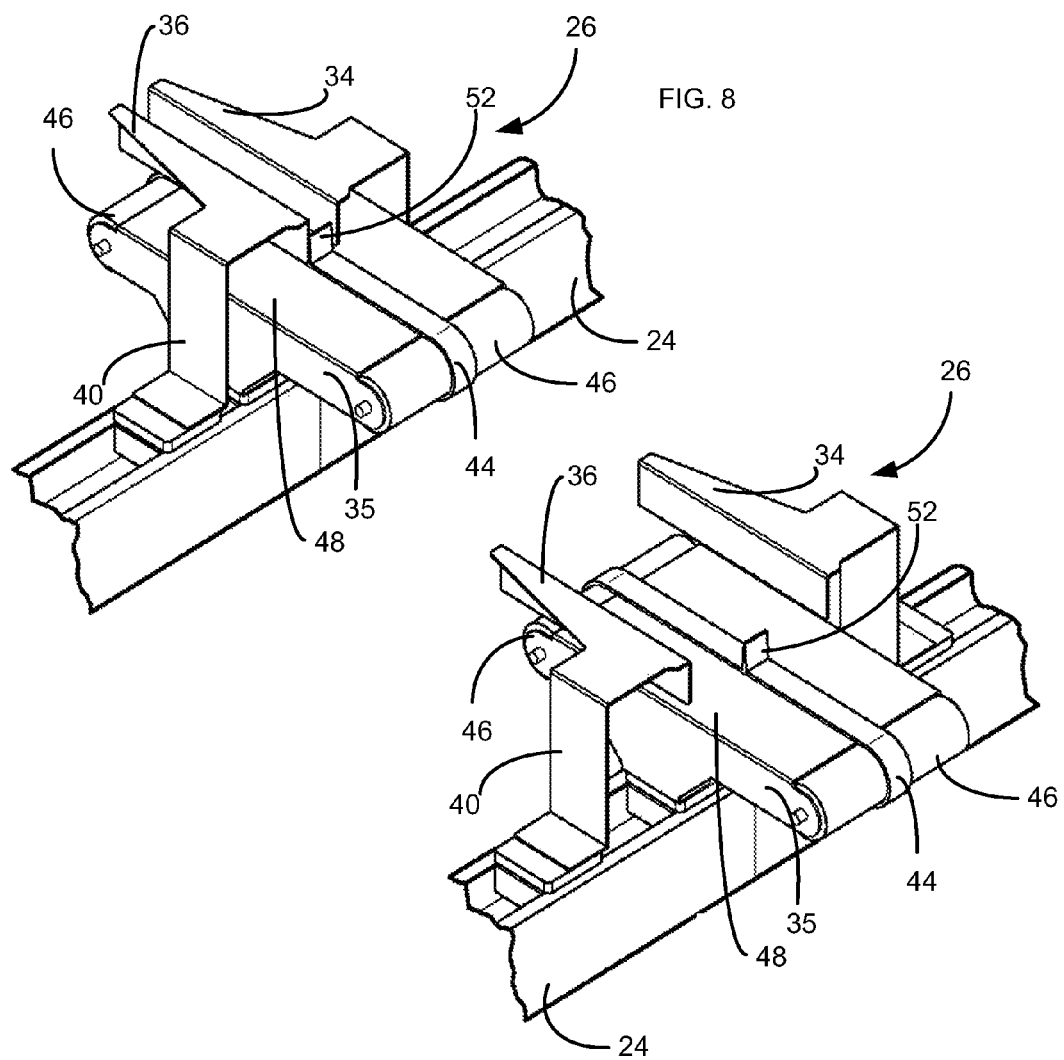
FIG. 8 is a perspective view of the carrier with a guide mechanism in an open position.
FIG. 8A is a perspective view of the carrier with the guide mechanism in a closed position.
Figure 9:
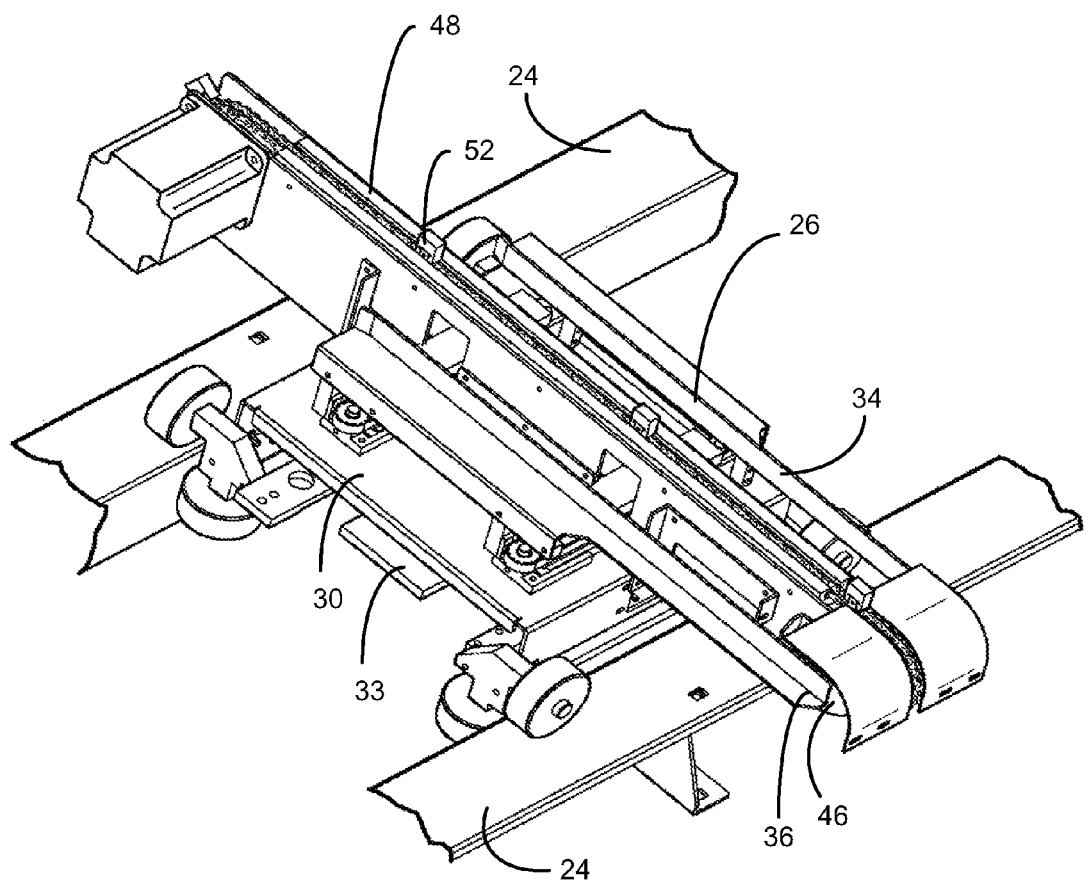
FIG. 9 is a perspective view of another embodiment of the carrier with a conveyor unit.
Figure 13:
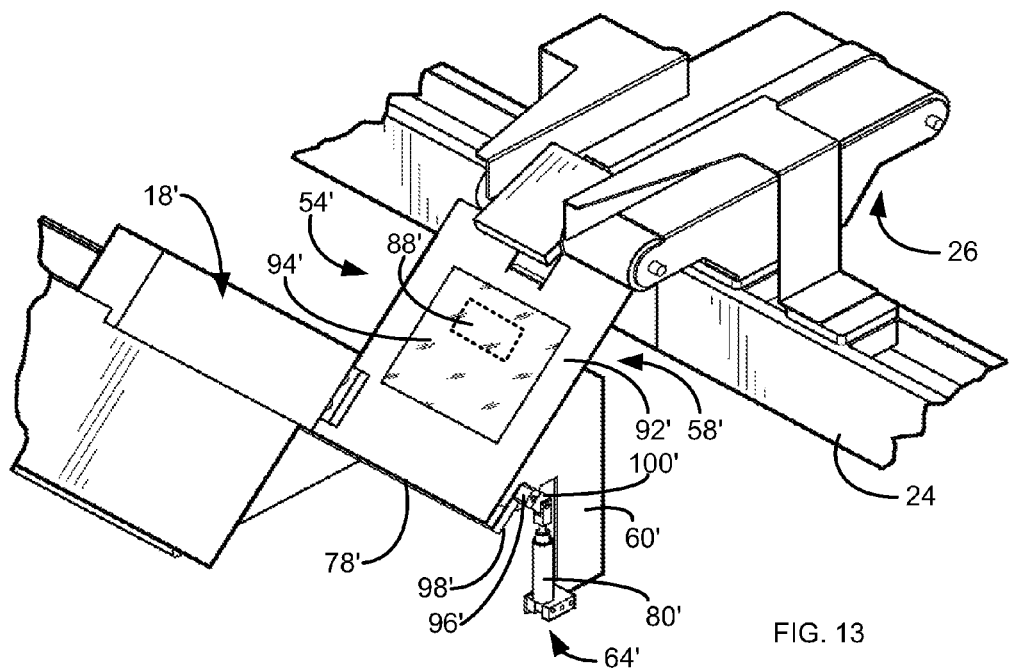
FIG. 13 is a perspective view of the carrier and the discharge guide assembly with a housing of the linear dispensing unit removed.
Figure 14:
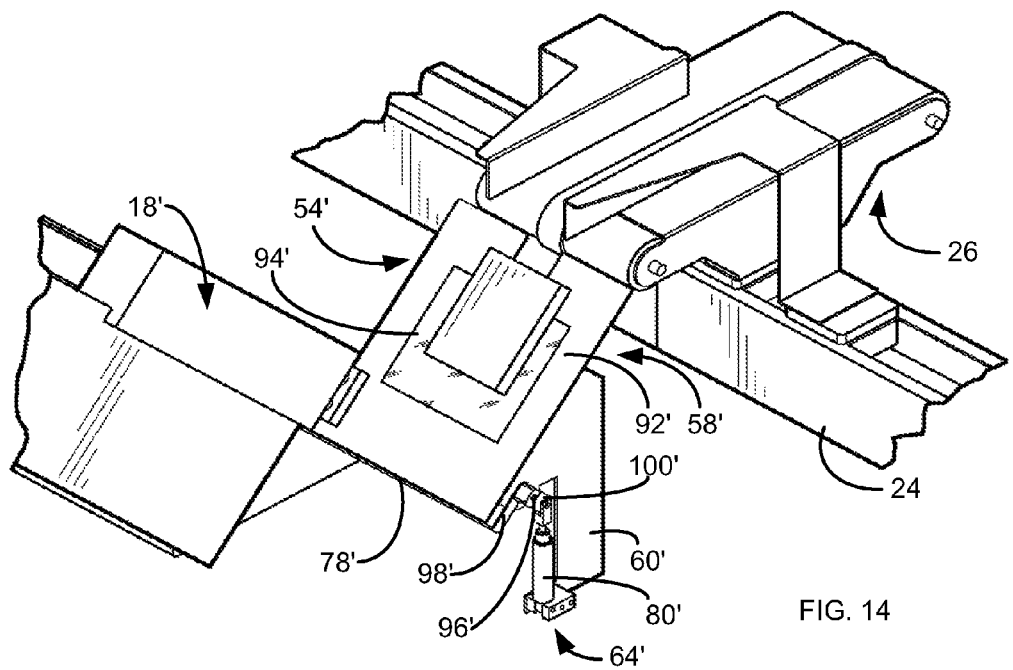
FIG. 14 is a perspective view of the carrier and the discharge guide assembly with a housing of the linear dispensing unit removed.

Referring now to FIGS. 8-9, the conveyor unit 35 includes a belt 44, a plurality of rollers 46, a plate member 48 and a conveyor actuator (not shown). The belt 44 encircles the rollers 46 and the plate member 48. At least one roller 46 is disposed at opposing ends of the plate member 48. An outer surface of the roller 46 frictionally engages the belt 44 while the roller 46 rotates about an axis to cause movement of the belt 44 about the plate member 48. The conveyor actuator is linked to the at least one roller 46 to cause it to rotate, thereby causing the belt 44 to rotate about the plate member 48. The conveyor actuator preferably includes a stepper motor to provide accurate movement in small intervals. The belt 44 includes one or more picker members 52 that are fixed to the belt 44. Each picker member 52 includes a finger-like member extending outwardly and substantially orthogonal or perpendicular to the belt 44. A free end of the picker member 52 contacts the inventory product as the belt 44 rotates and pulls the inventory product onto the plate member 48. The picker member 52 also functions as a stabilizer for the inventory product at an end or side not stabilized by the first and second guide members 34, 36, as best shown in FIGS. 7 and 13. The picker member 52 also functions as a divider between two inventory products in the event that the conveyor unit 35 picks two or more products, either from the same channel 10, or different channels 10.

Figure 4:
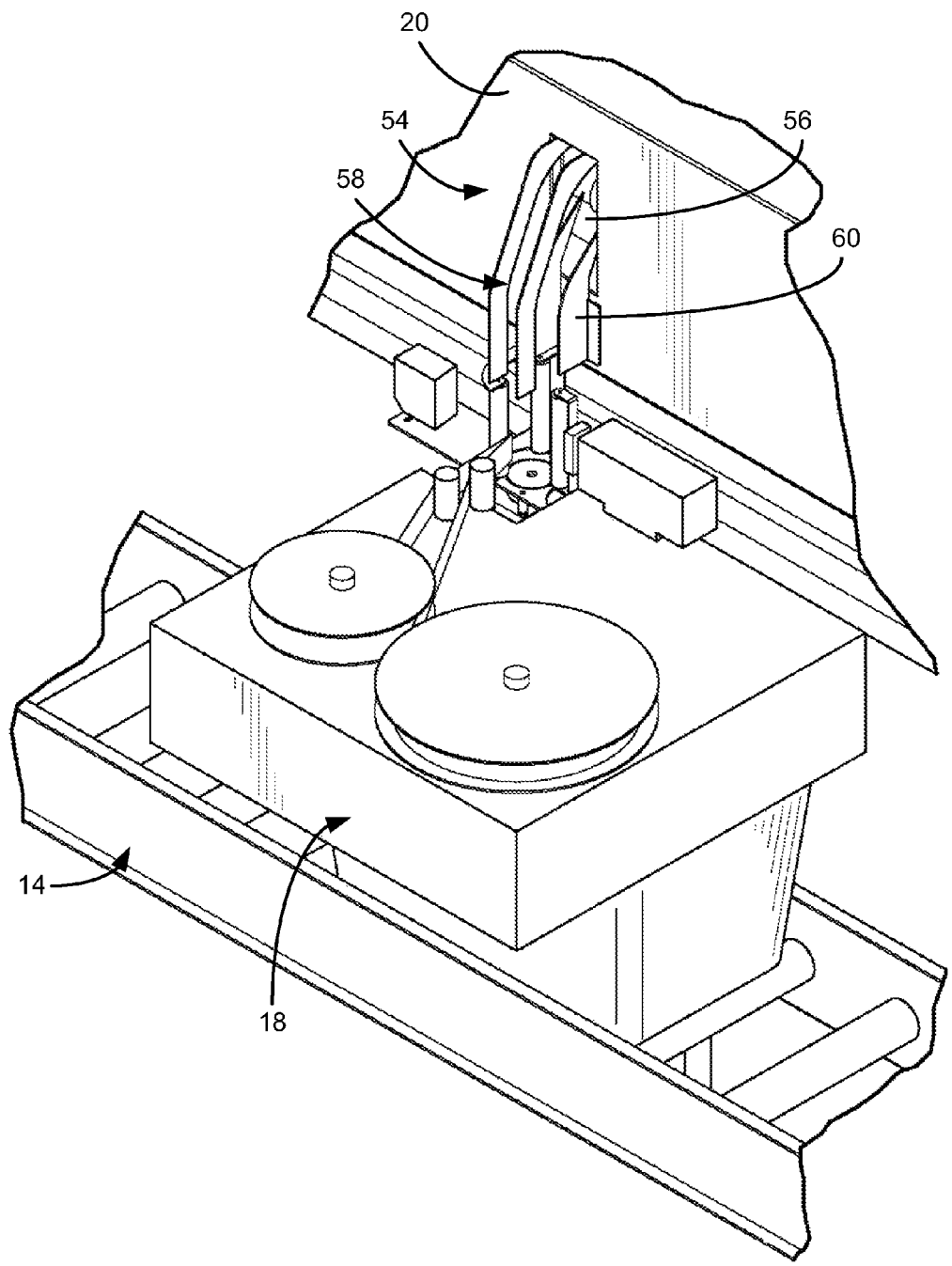
FIG. 4 is a perspective view of a labeler module and discharge guide assembly of a first embodiment.
Figure 5:
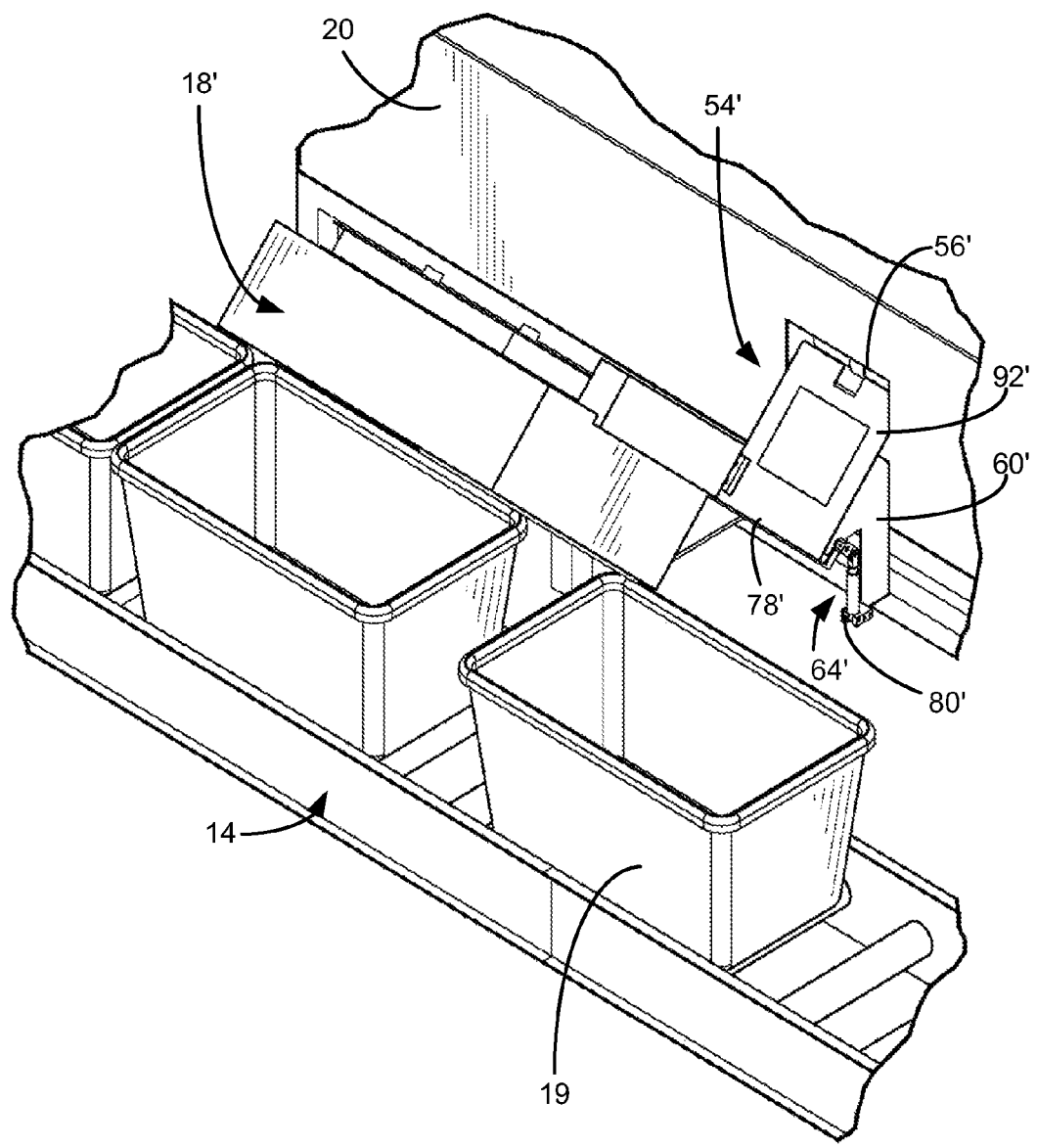
FIG. 5 is a perspective view of a labeler module and discharge guide assembly of a second embodiment.
Figure 6:
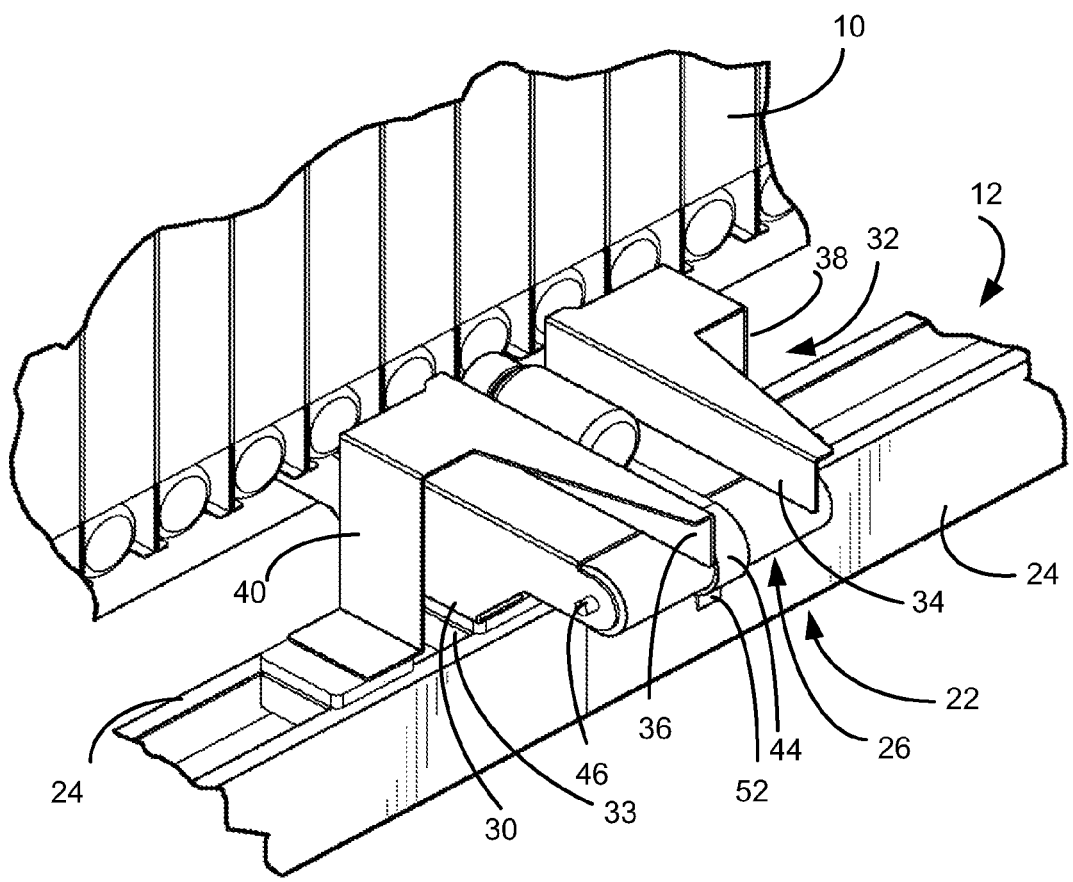
FIG. 6 is a perspective view of a carrier of the linear dispensing system guiding a cylindrical inventory product.
Figure 10:
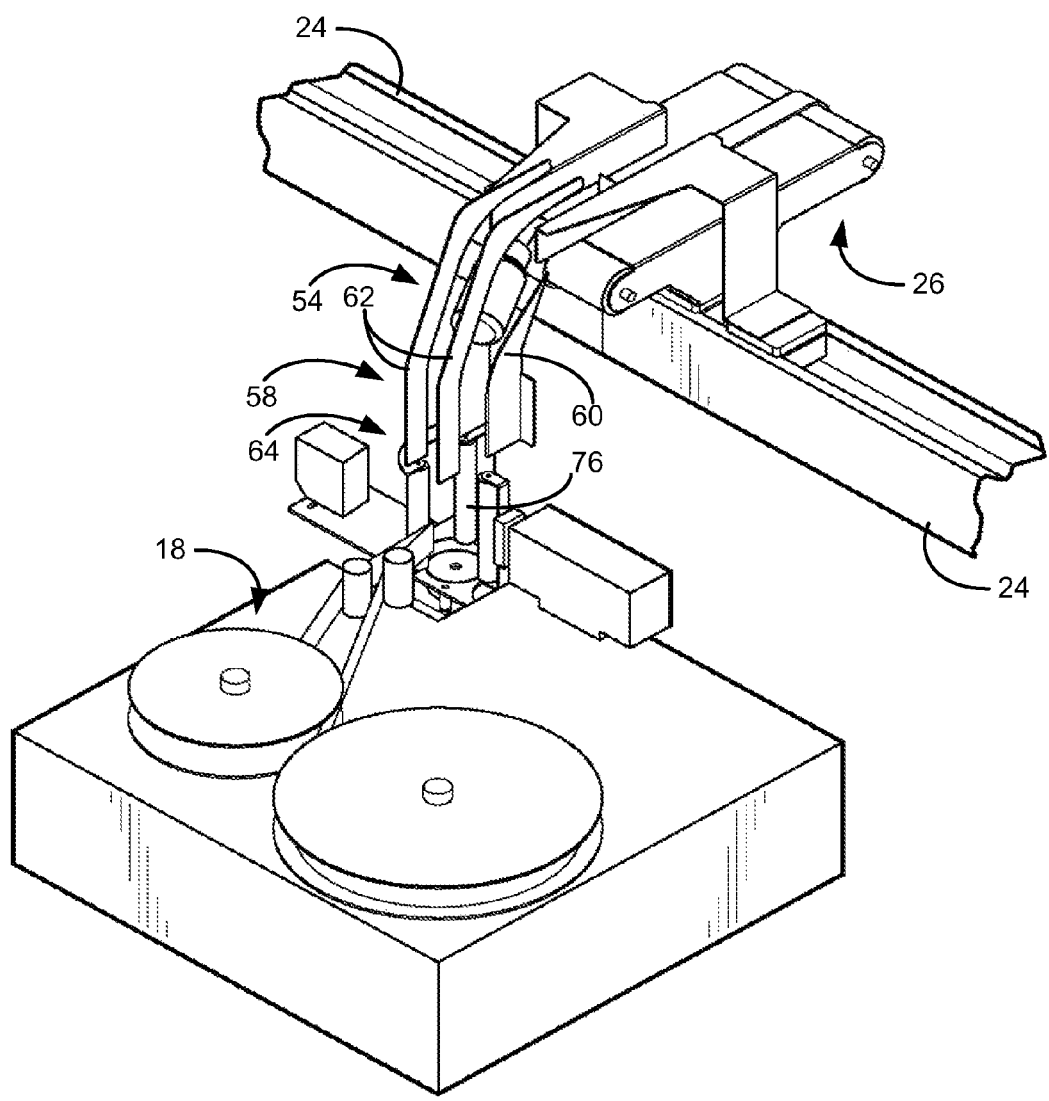
FIG. 10 is a perspective view of the carrier and the discharge guide assembly with a housing of the linear dispensing unit removed.

Referring to FIGS. 4, 5 and 10, the linear dispensing unit 2 further includes a discharge guide assembly 54 that receives the inventory product and guides it to the labeler module 18. More particularly, the discharge guide assembly 54 shown in FIGS. 4 and 10 are for bottle-type products and the discharge guide assembly of FIG. 5 is for a box-type product. The discharge guide assembly 54 generally includes a discharge aperture 56, a product feeder portion 58 and a support portion 60. The discharge aperture 56 is formed in the housing 20 of the linear dispensing unit 2 at strategic locations to provide the most efficient ejection point based on the number of carriers 26, the number of channels 10 and length of track 22. The product feeder portion 58 is disposed at the discharge aperture 56 and works in conjunction with the support portion 60 to direct the inventory product downwardly following ejection. As shown in FIG. 4, the support portion 60 is connected to an exterior of the housing 20 below the discharge aperture 56 to provide support for the inventory product as it is downwardly directed. As further shown in FIG. 10, the product feeder portion 58 includes feeder members 62 that extend from inside the housing 20, through the discharge aperture 56, and curve downwardly toward the labeler module 18. Thus, in the embodiment, shown in FIGS. 4 and 10, the product feeder portion 58 and the support portion 60 cooperatively form a chute for downward sliding reception of the cylindrical inventory product.

Figure 11:
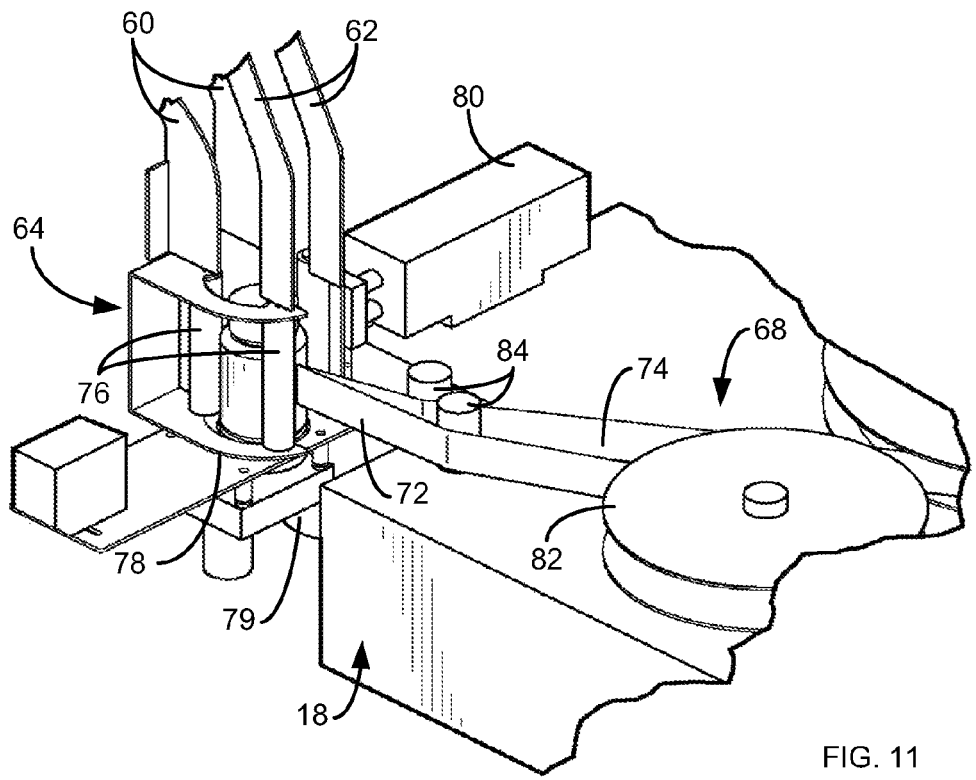
FIG. 11 is a perspective view of a stabilizer mechanism of the labeler module stabilizing a product.
Figure 12:
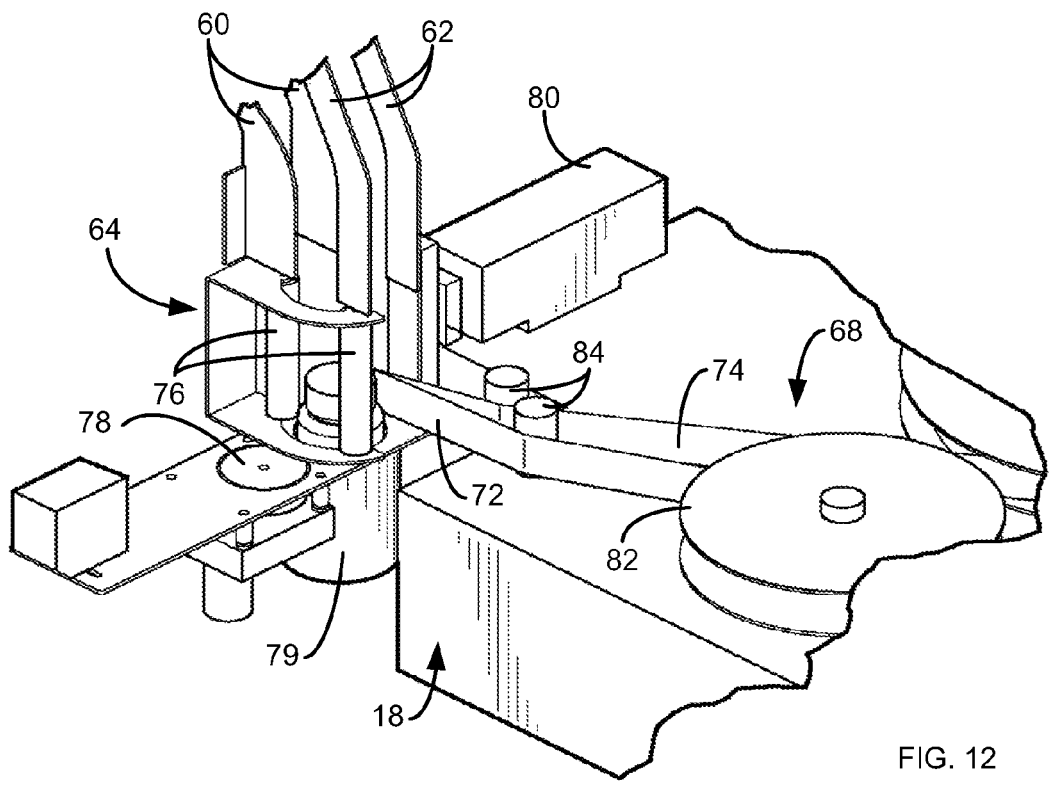
FIG. 12 is a perspective view of the stabilizer mechanism of the labeler module releasing the product.

Referring now to FIGS. 4, 11 and 12, the labeler module 18 for a bottle-type product is disposed at an exit of the chute formed by the product feeder portion 58 and the support portion 60. The labeler module 18 includes a stabilizer mechanism 64, a printer component 66, a label apparatus 68 and a label management unit 70. The stabilizer mechanism 64 receives the inventory product from the discharge guide assembly 54 and then secures the inventory product for application of a label 72. The printer component 66 includes a printer device that prints information, such as product information, directions for use of product, manufacturer identification and patient information, onto the label 72. The label apparatus 68 stores label stock 74 and is linked with the printer component 66 and the label management unit 70 to feed, upon demand from the label management unit 70, the label stock 74 to the printer component 66 for printing. The label apparatus 68 also applies the printed label 72 to the product.

The stabilizer mechanism 64 is configured to maintain the inventory product in the same spatial orientation as it was received. The stabilizer mechanism 64 includes a plurality of stabilizer fingers 76, a stabilizer plate 78 and one or more stabilizer actuators 80. One or more of the stabilizer fingers 76 is fixed at a location below the discharge guide assembly 54 while one or more stabilizer fingers 76 is movably disposed at the stabilizer actuator 80. The stabilizer mechanism 64 forms a cavity that is substantially aligned with the chute of the support portion 60 and the feeder members 62. Following ejection, the inventory product falls through the chute and into the cavity. The fixed stabilizer fingers 76 are disposed at a perimeter of the cavity while the stabilizer plate 78 provides underlying support. The stabilizer actuator 80 includes an arm with one of the stabilizer fingers 76 at an end portion of the arm. The stabilizer actuator 80 selectively engages the inventory product by applying pressure to the inventory product via the stabilizer finger 76. By extending the arm with the attached stabilizer finger 76, the stabilizer actuator 80 presses the inventory product against the fixed stabilizer fingers 76. In this embodiment, the stabilizer fingers 76 are tubular members and are substantially vertical to extend along the height of the inventory product. In one embodiment, the stabilizer actuator 80 is a guided dual rod pneumatic actuator, such as that from SMC Corporation of America, Noblesville, Ind. When the inventory product is stabilized by the stabilizer mechanism 64, the label apparatus 68 can apply the label 72. After adhering the label 72, the stabilizer actuator 80 retracts the arm to release the inventory product. The stabilizer plate 78 is slidably actuated by another stabilizer actuator (not shown) underneath the inventory product to either provide support for the inventory product or to release the inventory product. The actuator shifts a release aperture 79 of the stabilizer plate 78 directly underneath the inventory product, thereby releasing the product. The inventory product is then free to leave the cavity by falling under gravity through the release aperture 70.

The label apparatus 68 includes a storage unit 82 for storing the label stock 74 until needed, one or more roller guides 84 and a peeler 86 for peeling the label 72 from the label stock 74 and applying the label 72 to the inventory product. The label management unit, which may be incorporated into the control unit 8 of the dispensing system 2 or may be a separate control unit and is thus not shown, determines when the label apparatus 68 is needed and manages the outflow of label stock 74 from the storage unit 82 as well as instructs the printer component 66 with the proper data for appropriate labeling of the inventory product. The label management unit also commands the stabilizer actuator 80 and the actuator for the stabilizer plate 78. As described in more detail below, the label management unit may include a reader component disposed at the stabilizer mechanism 64 in order to read informational indicia on the inventory product that is necessary to configure the appropriate label 72 for the inventory product. The reader component may be any suitable imaging device such as an optical reader, scanning device or camera. For example, the reader component reads an original manufacturer's name or barcode and transmits such information to the label management unit that may, in turn, provide such information to the computer 4 for analysis. The computer 4 may include a memory unit for storing programs and a processor to execute programmed instructions in response to the information from the label management unit and provide one or more instructions to the label management unit for application of the label to the product.

As mentioned above, the computer 4 has access to one or more databases 7 that are populated with label information for printing on the label 72. The label information can include patient information, directions, drug reactions, name and location of dispensing entity, etc. The computer 4 (or control unit 8 in some embodiments) matches manufacturing information, read from the inventory product, with the identity of the patient in need of a dispensed product. The computer 4 then sends the label information and the patient's ID information to the label management unit. The label management unit then instructs the printer component 66 to print the supplied information onto the label stock 74 and instructs the storage unit 82 to feed additional label stock 74.

The reader component may also include a scanning feature to scan and capture an image of the product before and after the printed label 72 is placed on the inventory product. The images are transmitted to the computer 4 for verification processing and/or storage. In the verification processing, the computer 4 obtains the information printed on the label 72 and the manufacturer's information on the inventory product from the scanned image. The information is cross checked by the computer 4 with original information in the database 7 to ensure accuracy. If the computer 4 determines a discrepancy between the printed label 72 and the information stored in the database 7, the computer may send an alert message to the user-interface 6 to alert an operator of the system. In another embodiment, the computer 4 may provide the alert over the network 5 to a remotely located operator.

Referring now to FIGS. 1, 5 and 13-16, an additional embodiment of the labeler module 18 and the discharge guide assembly 54 is illustrated. The descriptions of the parts of the second embodiment identical to the parts of the first embodiment are omitted for the sake of brevity. The parts of the second embodiment are indicated with a prime ('). In this embodiment, the discharge guide assembly 54' is configured for non-cylindrical inventory products. Such products may be of virtually any size and/or shape, such as, for example, bottles, boxes and irregularly shaped packages and items, including tubes and devices. As shown in FIGS. 5 and 13-16, the discharge guide assembly 54' includes a discharge aperture 56', a support portion 60' and a product feeder portion 58' having a slide plate 92'. The slide plate 92' is disposed at an angle on the support portion 60' for directing the non-cylindrical inventory product to the labeler module 18' at an angle. The slide plate 92' includes a glass portion 94' integrally disposed on the slide plate 92' to provide a transparent portion for collecting information from a label. A reader component 88' is disposed behind the glass portion 94' of the slide plate 92' to read the manufacturer's information and scan images of the inventory product before and after labeling. As shown in more detail below, a plurality of reader components 88' may be incorporated into the assembly to read multiple sides of the product.

The stabilizer mechanism 64' of the labeler module 18' includes a stabilizer plate 78' pivotally attached to the support portion 60' via a pin at a pivot point 96'. In this embodiment, the stabilizer plate 78' has at least one fixed arm 98' that is fixed at an end portion of the stabilizer plate 78'. The fixed arm 98' has a pivoting end portion that is pivotably attached to the support portion 60' at the pivot point 96'. The stabilizer mechanism 64' further includes a stabilizer actuator 80' and at least one pivot arm 100' fixedly attached to the fixed arm 98' and rotatable about the pivot point 96' via the pin. The stabilizer actuator 80' is pivotably attached to the pivot arm 100' at a distance from the pivot point 96'.

In use, the stabilizer actuator 80' extends and retracts a piston rod to rotate the pivot arm 100' which pivots the stabilizer plate 78' about the pivot point 96'. The stabilizer plate 78' is rotated to either a support position or a release position by the stabilizer actuator 80'. In the support position, the piston rod of the stabilizer actuator 80' is retracted and the stabilizer plate 78' provides support for the non-cylindrical inventory product, as it rests on the slide plate 92'. In the release position, the piston rod of the stabilizer actuator 80' is extended such that the stabilizer plate 78' no longer supports the non-cylindrical inventory product, thereby allowing the non-cylindrical inventory product to slide off of the slide plate 92' by gravity.

Figure 15:
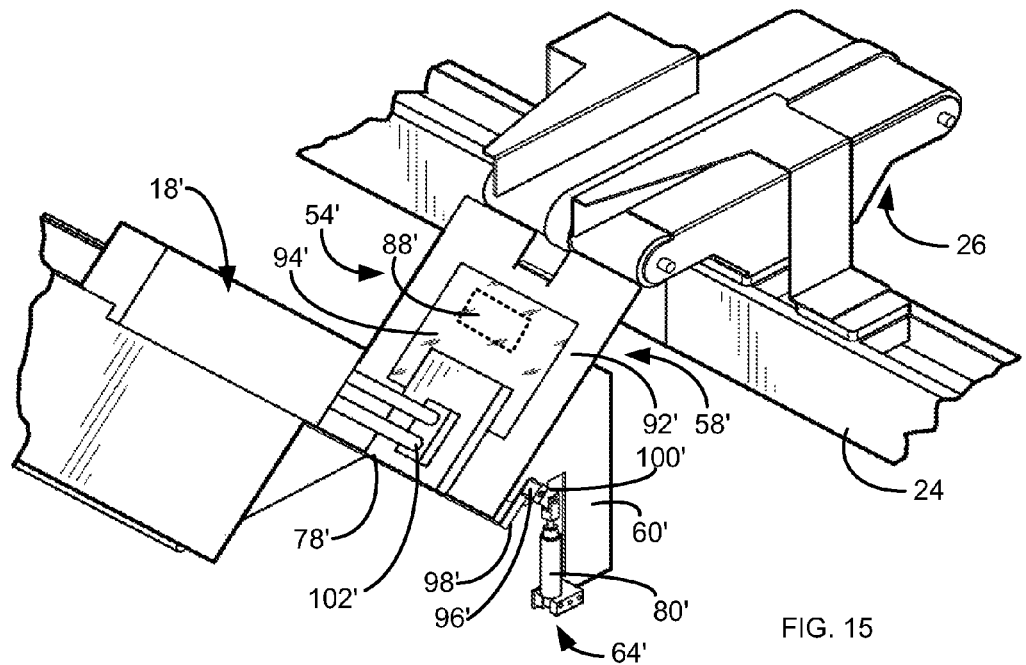
FIG. 15 is a perspective view of a label applied to the product with a stabilizer plate in a support position.
Figure 16:
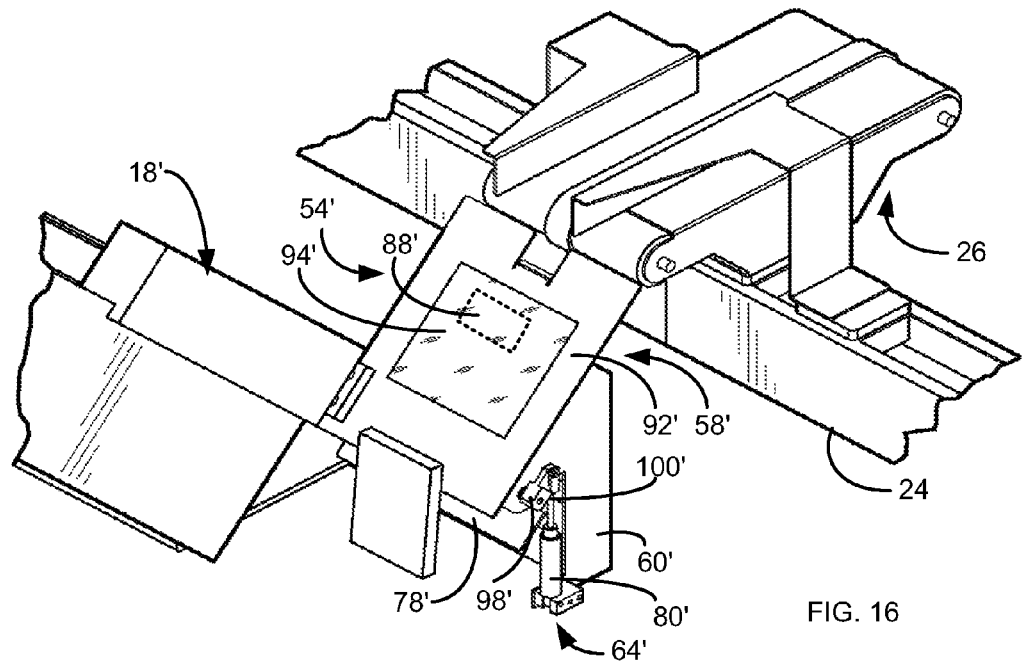
FIG. 16 is a perspective view of the product released with the stabilizer plate in a release position.

The labeler module 18' for non-cylindrical products is operatively disposed at the exterior of the housing 20 at an angle to print and apply the label 72 while the inventory product rests on the stabilizer plate 78' and the slide plate 92'. The labeler module 18' of the present embodiment is generally similar to the above-described labeler module 18. A notable difference, however, is the orientation and use of an actuator 102', as shown in FIG. 15. Specifically, the actuator 102' extends an arm toward the slide plate 92' to apply or stamp the label 72 onto the inventory product. The actuator 102' then retracts the arm for application of the next label 72. Further, as shown in FIG. 16, after the label 72 is applied to the product, the stabilizer plate 78' is rotated to allow the product to slide off the slide plate 92' and into a tote for further processing.

Figure 17:
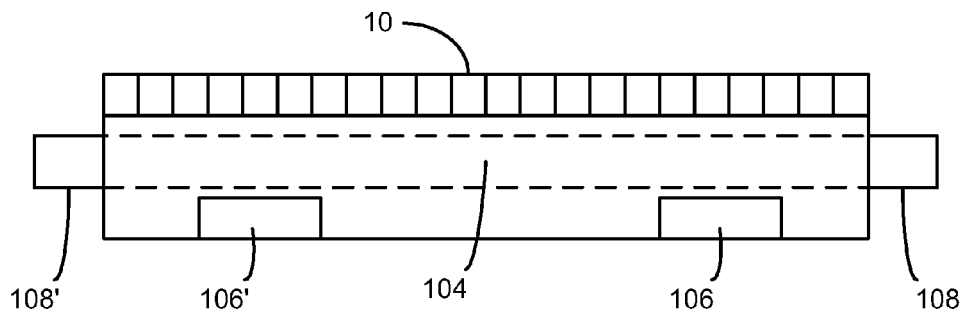
FIG. 17 is a block diagram of regions of the linear dispensing unit.

Referring now to FIG. 17, the area occupied by the linear track assembly 12 is categorized into regions. The largest region, a picking region 104, is an area in which the carrier 26 picks inventory products from the channels 10 for delivery to the discharge guide assembly 54, 54'. Within the picking region 104 are designated discharge regions 106, 106' for ejecting the inventory product through the discharge aperture 56, 56'. For each discharge aperture 56, 56', a discharge region 106, 106' is assigned. Thus, each discharge region 106, 106' is configured for ejection of a non-cylindrical inventory product, a cylindrical inventory product, or both. In this embodiment, the discharge region 106 is for ejection of cylindrical inventory products to the labeler module 18 via the discharge guide assembly 54 and the discharge region 106' is for ejection of non-cylindrical inventory products to the labeler module 18' via the discharge guide assembly 54'. In other embodiments, however, a single or universal discharge region 106 may be provided for any type and shape of product. The area of the linear track assembly 12 further includes one or more home regions 108, 108' for one of the carriers 26 to occupy and avoid conflict with other carriers 26. Preferably, the home region 108, 108' is disposed at an end portion of the linear track assembly 12 to provide the greatest possible space for other carriers 26. The locations of the regions 104, 106, 106', 108, 108' as they relate to positions along the linear motor modules 28 are stored by the control unit 8 for use when commanding the linear motor modules 28 to move the carriers 26 toward various locations along the linear track assembly 12. More particularly, the control unit 8 may indicate one end of the linear track assembly 12 as a reference point, such as home end 108. Each position along the track assembly 12 may be in relation to the reference point. For example, the linear track assembly 12 may be 8 meters long measured in millimeter increments from the reference point. As such, any position along the track may be indicated by the control unit 8 as a number of millimeters from the reference point. As should be appreciated, the reference point may be any point along the linear track assembly 12 and the track may be divided into any measurement of the overall length of the track to provide a reference for any position along the track. As explained in more detail below, such a reference position may allow the control unit 8 and/or computer 4 to determine which product is located in which channel 10.

In general, the control unit 8 in conjunction with the computer 4 coordinates independent movement of the carriers 26 along the linear track assembly 12. The linear motor modules 28 communicate with the control unit 8 for transferring the carriers 26 from one linear motor module 28 to an adjacent linear motor module 28. Thus, the carriers 26 may simultaneously or substantially simultaneously pick inventory products from the channels 10. For example, the carrier 26 that picks a cylindrical inventory product transports it to the discharge aperture 56 which may create space for another carrier 26 to pick a non-cylindrical inventory product and transport it to the discharge aperture 56'. This coordinated independent movement is also advantageous when there is a single discharge aperture 56 or 56' because the control unit 8 controls the movement of each carrier 26 to share an ejection point and make space for other carriers 26.

The control unit 8 preferably includes a microcomputer with control programs that control the linear motor module 28 and the label management unit 70. The control unit 8 can also include other conventional components such as an input interface circuit, an output interface circuit, storage devices such as a ROM (Read Only Memory) device and a RAM (Random Access Memory) device. The memory circuit stores processing results and control programs such as the ones for the linear motor module 28 and the label management unit 70 operation that are run by a processor circuit. The control unit 8 is operatively coupled to the linear motor module 28 and the label management unit 70 in a conventional manner, such as via a data bus or wireless communication. The control unit 8 is capable of selectively controlling the linear motor module 28 and the label management unit 70 in accordance with the control program or from instructions or commands provided by the computer 4 and/or the user interface 6. It will be apparent to those skilled in the art from this disclosure that the precise structure and algorithms for the control unit 8 can be any combination of hardware and software that will carry out the functions of the present invention.

In use, an operator assigns each type of inventory product to its respective channel 10. The walls of the channels 10 are adjusted as may be necessary to hold the inventory products in a desired orientation. As explained in more detail below, the operator then enters the width of the channels 10 into the user interface 6 for use by the control unit 8 which associates the channel with a position along the linear track assembly 12. After the operator loads the channels 10 with the inventory product, the quantity of product within the channel 10 is entered into the user interface 6. A "low level" threshold can be predetermined and set by the operator via the user interface 6. As also explained below, the control unit 8 utilizes one or more sensors to monitor the quantity of product for any channel 10 to prevent exhaustion of the inventory products in the channels. As the carriers 26 pick and eject inventory products, the control unit 8 monitors the inventory sensors and transmits an alert if the quantity drops below a predetermined threshold.

The same or different operator may enter parameters and commands into the user interface 6 and/or computer 4 to supply to the control unit 8 information regarding location of individual channels 10 along the linear track assembly 12, type of inventory product in the individual channels 10, patient lists, prescriptions, quantities, etc. Alternatively, the computer 4 may retrieve some of such information from the database 7 or over the network 5. The control unit 8 then commands the linear motor modules 28 to move the carriers 26 to desired locations along the linear track assembly 12. Using the knowledge of the width of the channel 10, the control unit 8 commands the guide actuator of the guide mechanism 32 to space the first and second guide members 34, 36 apart to substantially the same width as the channels. Once the carrier is in place, the control unit 8 then commands the conveyor actuator of the conveyor unit 35 to rotate the belt 44 around the plate member 48 by rotating the roller 46. The conveyor actuator rotates the roller 46 until the picker member 52 on the belt 44 pulls the inventory product onto the plate member 48 from the channel 10. At this point, the inventory product is secure on the conveyor unit 35 among the first and second guide member 34, 36 and the picker member 52 in the same (or substantially the same) orientation as in the channel 10. In some embodiments, the conveyor unit 35 may select and carry multiple products at a time, such as three of the same or varying products.

In response to a command by the control unit 8, the linear motor module 28, which is underneath the carrier 26, moves the carrier 26, via electromagnetic force, to the discharge areas 106, 106'. Passing of the carrier 26 to another linear motor module 28 may occur as detailed below. The control unit 8 again commands the conveyor actuator to rotate the roller 46, which drives the belt 44 around the plate member 48 such that friction from the belt 44, as well as the picker member 52, shift the inventory product off the plate member 48. While shifting is occurring, the guide members 34, 36 direct the inventory product toward the discharge guide assembly 54, 54'. The inventory product then falls or slides through the discharge guide assembly 54, 54' into position for labeling, while still having the same orientation as when oriented in the channel 10.

In the case of the cylindrical inventory product, the labeler module 18 stabilizes the inventory product by extending the arm of the stabilizer actuator 80 such that the attached finger presses the inventory product against the fixed stabilizer fingers 76. The control unit 8 supplies the necessary information for printing on the label stock 74 to the controller component 90, which drives the printer component 66. After application of the printed label 72 to the inventory product, the control unit 8 instructs the stabilizer actuator 80 to retract the arm. The control unit 8 also instructs the stabilizer actuator (not shown) to slide the stabilizer plate 78 laterally so that the release aperture 79 is directly underneath the inventory product. At this point, the inventory product is free to fall through the release aperture 79 and into one of the totes 19 of the receiving track assembly 14.

In the case of the non-cylindrical inventory product, the angled slide plate 92' provides a surface for the inventory product to slide downwardly to abut the stabilizer plate 78'. The control unit 8 supplies the necessary information for printing on the label stock 74 to the controller component 90. After application of the printed label 72 to the inventory product, the control unit 8 provides instructions for the stabilizer actuator 80' to extend the piston rod, thereby causing the stabilizer plate 78' to rotate downwardly into the release position. The inventory product is then free to slide off of the angled slide plate 92' and into one of the totes 19 of the receiving track assembly 14.

Figure 18A:
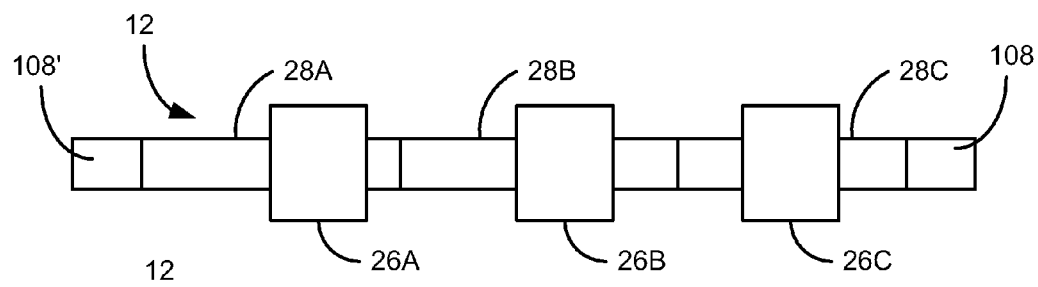
FIGS. 18A-18C are block diagrams of exemplary locations of carriers on linear motor modules in the linear dispensing unit.
Figure 18B:
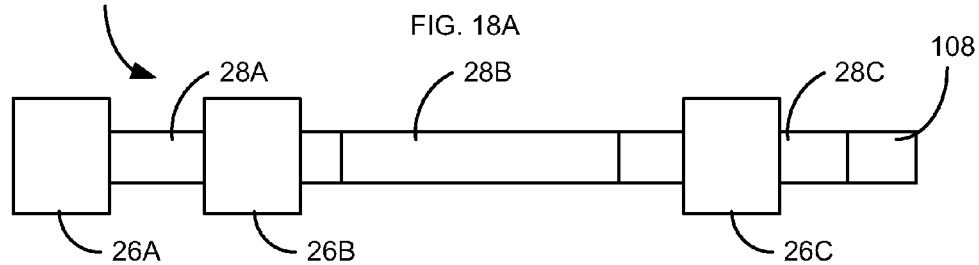
Figure 18C:
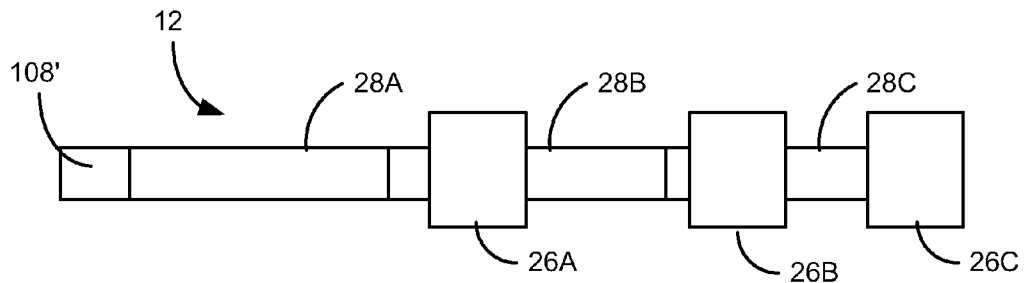

The linear dispensing system 1 efficiently manages many carriers 26 on a common network of any number of linear motor modules 28. Advantageously, accurate and continuous control of the carriers' 26 movement and interaction provides for accelerated and efficient dispensing of the inventory product by maintaining the same orientation for uniform labeling. This enables the system to process at least about 600-700 products per hour, for example. Referring to FIGS. 18A-18C, three linear motor modules 28a, 28b, 28c are disposed in the linear track assembly 12, which includes three carriers 26a, 26b, 26c. FIG. 18A illustrates each carrier 26 in its respective linear motor module 28. The control unit 8 can command carrier 26a to pick, transport and eject the inventory product from the channel 10 while the carrier 26b is picking or transporting and the carrier 26c is picking, transporting or ejecting the inventory product. The present disclosure provides a system 1 that allows carriers 26a, 26b, 26c to slide over any of the linear motor modules 28a, 28b, 28c for accelerated and efficient dispensing. The carrier 26a or carrier 26c may move to the home region 108, 108' to provide space along the linear track assembly 12. In FIG. 18B, carrier 26a is located at the home region 108' while carrier 26b, located in the discharge region 106', is now controlled by linear motor module 28a. After commanding the carrier 26b to pick a non-cylindrical inventory product from one of the channels 10, the control unit 8 ascertains that the carrier 26b must proceed to the discharge region 106' located in an area occupied by the linear motor module 28a. The control unit 8 commands the linear motor module 28a to move the carrier 26a to the home region 108', after which the linear motor module 28b is commanded to pass the carrier 26b over to the linear motor module 28a. In the situation shown in FIG. 18C, carrier 26c is at rest at the home region 108' while carrier 26a picks the inventory product from the channel 10 and carrier 26b ejects its cylindrical inventory product at the discharge region 106. It should be understood that the carrier 26b in the discharge region 106, 106'could be picking inventory since the carrier 26b is still located in the picking region 104, i.e. channels 10 are located opposite the carrier 26b from the discharge aperture 56.

Figure 19:
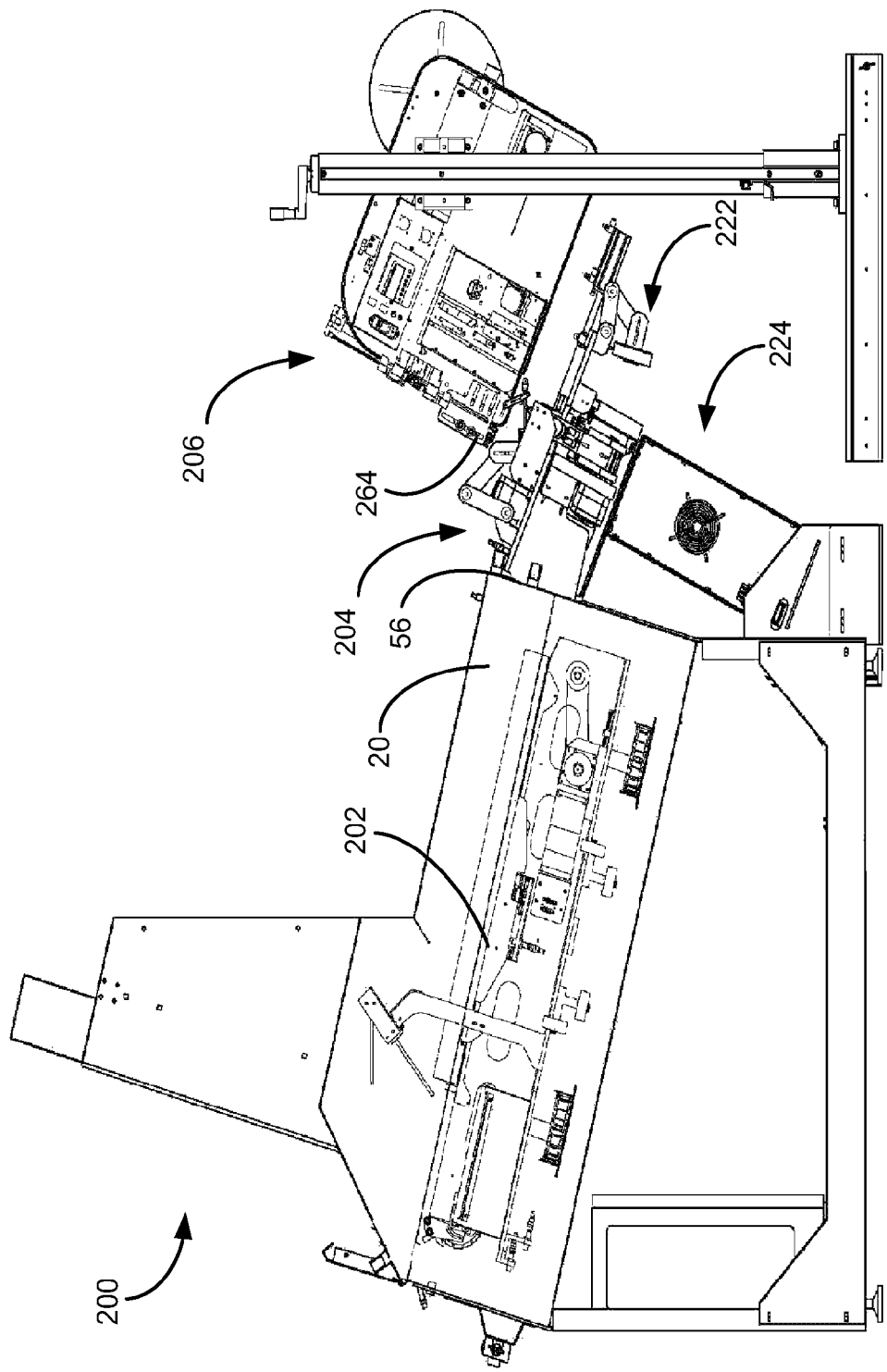
FIG. 19 is a side sectional view of an alternate embodiment of the linear dispensing system.

FIGS. 19-36 illustrate an additional embodiment of the linear dispensing system that is capable of receiving both cylindrical and non-cylindrical inventory products including flat-sides products and irregular products. As best shown in FIG. 19, the system 200 includes a multi-product carrier 202, a universal escapement assembly 204, and a flap-fold labeler module 206. The descriptions of parts of this embodiment that are identical to the parts of the embodiments described above are omitted for the sake of brevity.

Advantageously, the multi-product carrier 202 can obtain a plurality of inventory products from a plurality of channels without regard to the shape of the inventory products and transport them simultaneously to a single universal escapement assembly 204 for verification and labeling by the same labeler module 206. This eliminates the need to route cylindrical and non-cylindrical inventory product items to separate discharge guide assemblies 54 and 54' and labeler modules 18 and 18'.

The multi-product carrier or vehicle 202 (FIGS. 21 and 22) includes a base plate 208, above which is mounted a drive chain 210 passing over a pair of sprocket gears or sprockets 212. A plurality of spaced dogs or pickers 214 are connected to and extend outwardly from the drive chain 210. A pair of chain guards 215 is upstanding from the base on either side of the drive chain 210. The chain guards 215 also support respective product guides 216 (FIG. 22), which are connected to the carrier 202 and move with it. The distance between the product guides 216 may be adjusted by means of a guide adjustment mechanism, similar to the guide adjustment mechanism discussed above. The pickers 214 and the adjustable product guides 216 cooperatively partition the carrier into a series of product receiving zones 220. The illustrated carrier 202 includes a plurality of receiving zones, for receiving a plurality of products from one or more channel locations. Thus, it is foreseen that any number of zones may be provided for receiving a corresponding number of products. The carrier 202 traverses back and forth along the length of the linear dispensing unit 200 as previously described, using the pickers 214 to pick stored products from one or more selected product channels and then release them between the guides 216, which are adjusted to receive the products.

Figure 23:
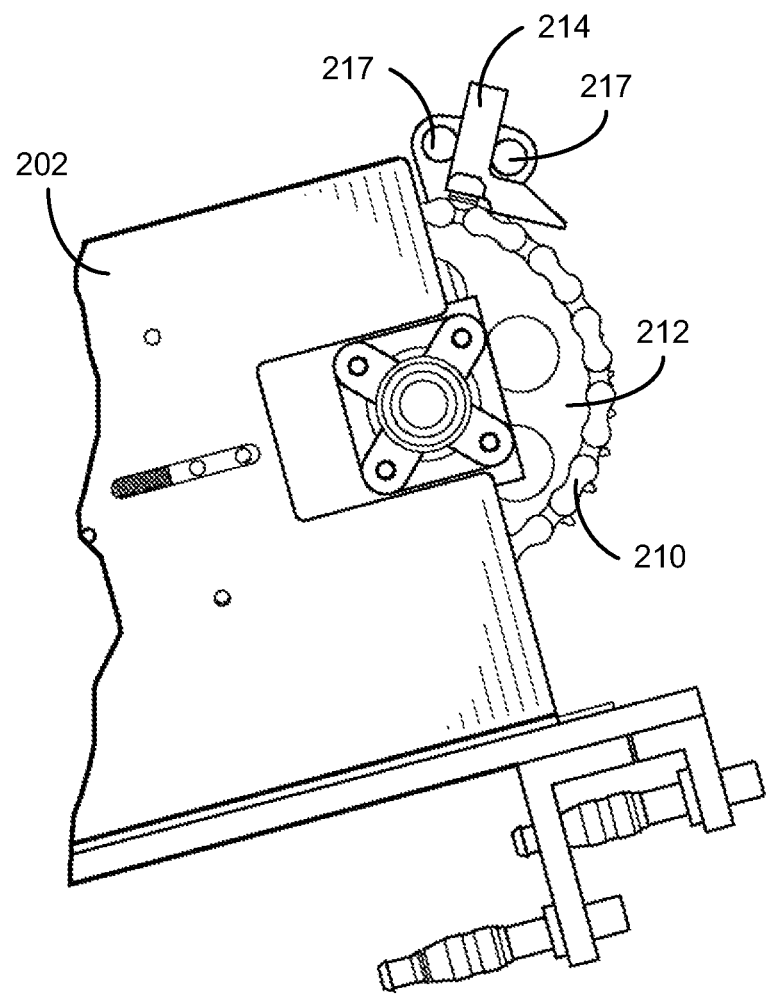
FIG. 23 is a side elevational view of the carrier showing the picker positioning sensors.

Several sensors are associated with the carrier 202 to provide various functions to the system 2. For example, as shown in FIG. 23, the carrier 202 may include a pair of picker alignment sensors 217. The picker alignment sensors 217 detect the presence of a picker 214 in front of the sensors. Thus, as the pickers 214 pass in front of the sensors 217 during activation of the drive chain 210, the movement and presence of the pickers is detected by the sensors. Two or more picker alignment sensors 217 are positioned and spaced accordingly such that a properly placed picker 214 may reside between the sensing field of the sensors. Prior to movement of the carrier 202 along the linear track 12, the control unit 8 may activate the carrier to rotate the pickers 214 until a picker is properly located between the two sensors 217. This position of the picker 214 between the sensors 217 indicates that pickers are properly aligned for movement of the carrier 202 along the linear track 12. In one embodiment, the drive chain 210 of the carrier 202 may be activated in either the forward or backward direction in response to the position information provided by the picker alignment sensors 217 until at least one picker 214 is properly placed between the sensors.

Figure 24:
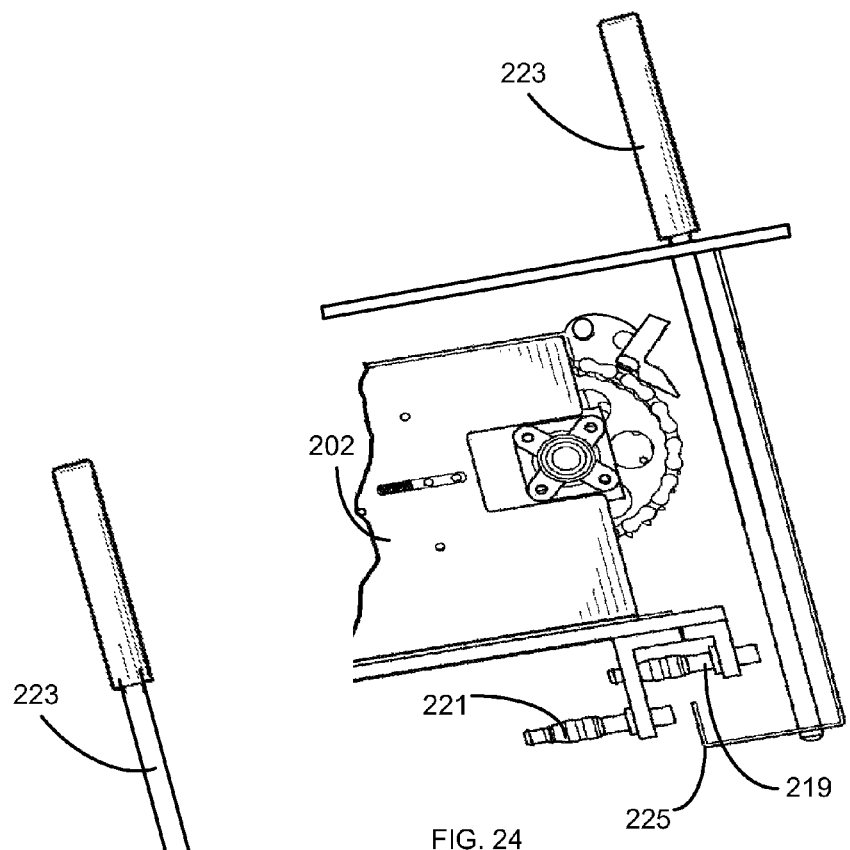
FIG. 24 is a side elevational view of the linear dispensing unit showing the channel alignment sensors in relation to a alignment rod.
Figure 25:
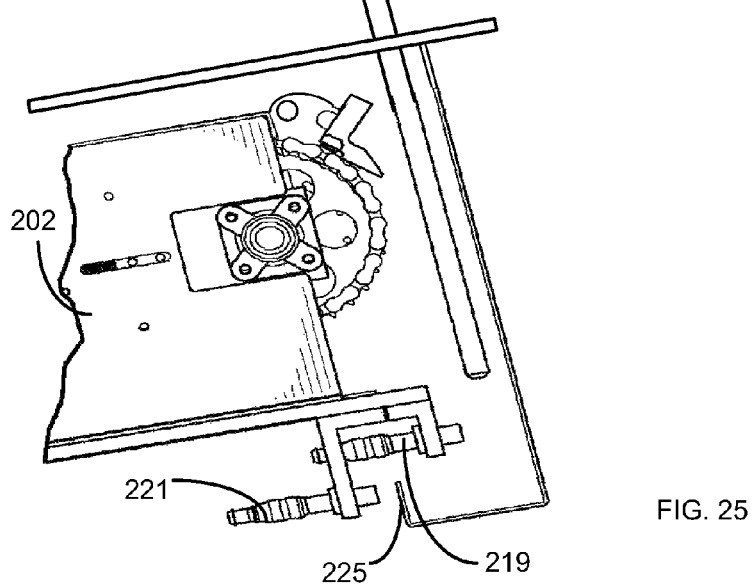
FIG. 25 is a side elevational view of the linear dispensing unit showing the channel alignment sensors with the alignment rod partially removed.

In another example shown in FIGS. 24 & 25, the carrier 202 may include a pair of channel alignment sensors 219, 221 that provide location information to the control unit 8 (and the computer 4) during initial population of a channel 10 with a product. As described above, the computer 4 or control unit 8 may associate a position along the linear track 12 with a channel 10 and the product located within that channel. To provide this information, an operator enters the width of the channel 10 into the user interface 6 for use by the control unit 8 which associates the channel with a position along the linear track assembly 12. After the operator loads the channel 10 with the inventory product, the channel location may then be initialized with the system. In one embodiment, the operator may utilize an initialization or alignment rod 223 and the initialization channel alignment sensor 219 to determine the location of the particular channel 10. As shown in FIG. 24, the alignment rod 223 is inserted along the back of the linear dispensing unit 2 through one or more initialization guide holes. Once properly seated in the initialization guide holes, the operator or control unit 8 begins an initialization process to associate a location along the track 12 with a channel 10. More particularly, the carrier 202 may move along the track 12 until the initialization channel alignment sensor 219 detects the alignment rod 223. Upon detection, the control unit 8 or computer 4 associates the position of the carrier 202 (such as a distance from a reference point as described above) with the channel 10 being initialized. In addition, the position of the carrier 202 may also be associated with any other information associated with the channel 10, such as product type, inventories, bar codes information, and the like. In this manner, the control unit 8 becomes aware of the position of any channel 10 and the product being dispensed from that channel.

Once the location is associated with a particular channel 10 using the alignment rod 223, the rod may be removed or withdrawn, either partially or completely, as shown in FIG. 25. Once all of the channels 10 in use are initialized, the control unit 8 may use the channel alignment sensor 221 to properly place the carrier 202 for selecting a product from a channel. For example, the carrier 202 may move along the track 12 as described above to a position associated with a particular channel 10 to select a product from that channel. However, because the location may be an approximate location depending on the spacing of the position locations, the carrier 202 may not be properly positioned below the channel 10. Thus, once near the location of the channel 10, the control unit 8 may incrementally move the carrier until the channel alignment sensor 221 detects the presence of the alignment tooth 225. The alignment tooth 225 may be a tab or finger extending into the detection area of the channel alignment sensor and aligned with the channel 10 such that once the carrier 202 aligns the channel alignment sensor with the alignment tooth, the carrier is in a proper position to retrieve a product from the channel. Thus, through the use of the initialization channel alignment sensor 219 and the channel alignment sensor 221, the carrier 202 may first locate the position of a channel 10 and be properly positioned beneath the channel for product removal.

Figure 26:
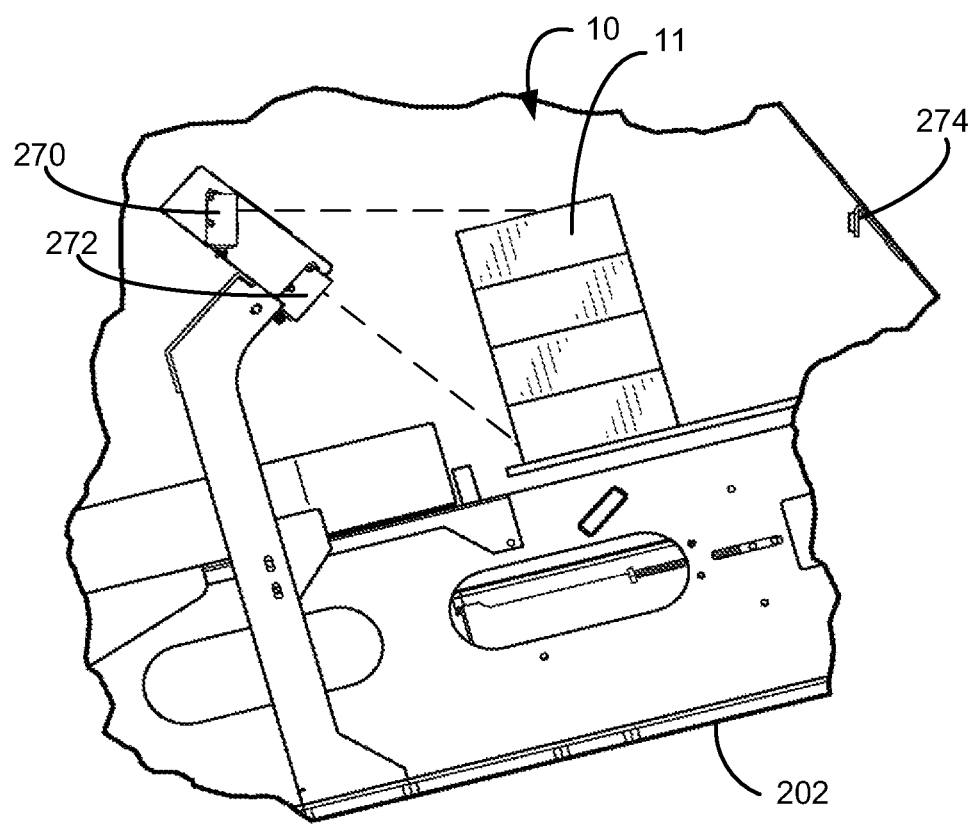
FIG. 26 is a side elevational view of the linear dispensing unit showing the product quantity sensors detecting the number of products in a channel.
Figure 27:
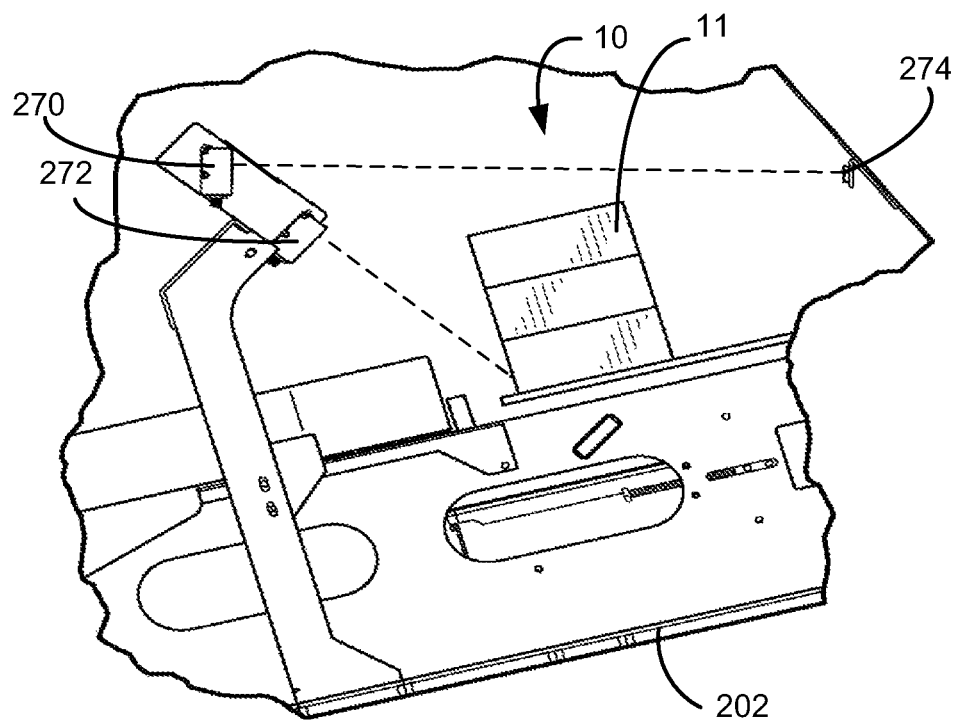
FIG. 27 is a side elevational view of the linear dispensing unit showing the product quantity sensors when the number of products in the channel is low.
Figure 28:
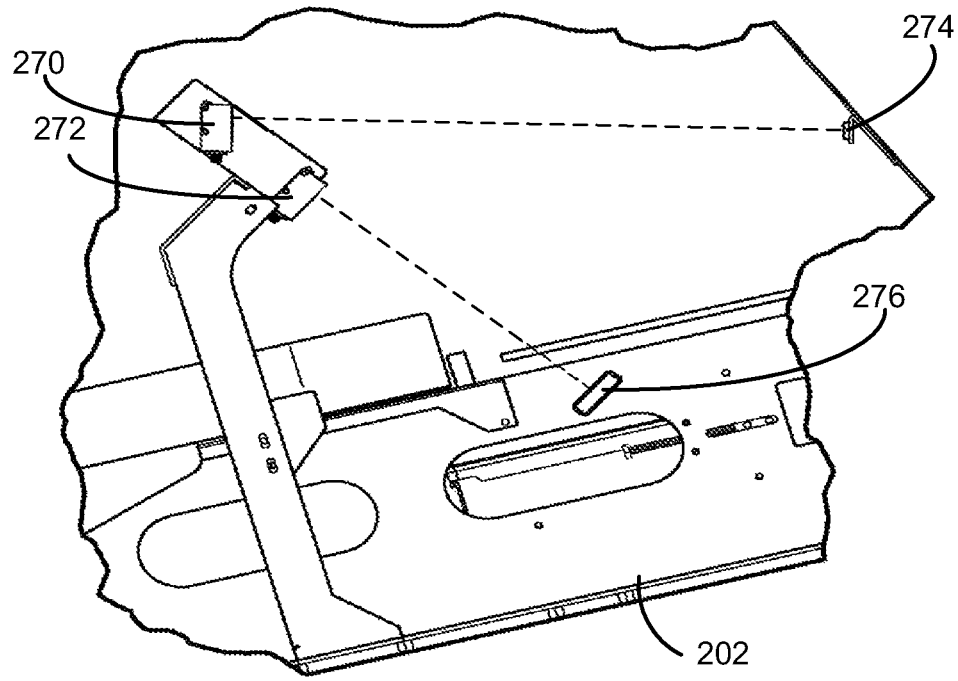
FIG. 28 is a side elevational view of the linear dispensing unit showing the product quantity sensors when the number of products in the channel is empty.

Several additional sensors may be associated with the carrier 202 to detect when the quantity of products in a channel 10 is low or empty. These product quantity sensors may be a laser sensor or other light emitting sensor that emits a beam of light that is reflected off a reflective surface back to the sensor. In general, the sensor detects when an object interrupts the reflected beam. As shown in FIGS. 26-28, the carrier 202 may include at least two product quantity sensors 270, 272 oriented to detect when a product 11 in a channel 10 is low and when a channel is empty. The low product quantity sensor 270 may be associated with the carrier 202 and oriented such that the emitted light beam points into the channels 10 at a particular height within the channels. A low product reflective surface 274 is located behind the channels 10 such that the channels 10 are situated between the low product quantity sensor and the low product reflective surface. In operation, the control unit 8 may activate or retrieve information from the low product quantity sensor 270 when the carrier 202 is oriented to select a product 11 from a particular channel 10. During or after selection of the product 11, the control unit 8 determines if the low product quantity sensor 270 detects the reflected emitted beam, thereby indicating that product is low in that particular channel 10. For example, as shown in FIG. 27, the low product quantity sensor 270 is oriented to detect when the number of products 11 in the channel 10 is less than four remaining products. In this example, the emitted beam is reflected back to the low product quantity sensor 170 and a signal is provided by the sensor to the control unit 8 to indicate that the channel 10 is low on product 11. In response, a notification or warning signal may be provided by the control unit 8 to the computer 4 or user interface 6 to notify or warn a technician to refill the product 11 in that channel 10. Such an analysis may be performed each time a product 11 is picked or it may be performed routinely to verify the number of products in the channels 10. Further, it should be appreciated that the low product quantity sensor 270 may be located at any height relative to the channel 10 to detect when the number of products 11 in the channel is below any number.

In a similar manner, an empty product quantity sensor 272 may indicate when a channel 10 has no more available products 11 in the channel. The empty product quantity sensor 272 may be angled in a manner to emit a beam through a floor support of the channel 10 so that the presence of a product 11 against the channel floor support interrupts the beam. Thus, as shown in FIG. 28, the beam may pass through the channel floor support when no products 11 remain in the channel 10. Similar to the previously described example, an empty product reflective surface 276 may reflect the beam back to the empty product quantity sensor 272. In one embodiment, the empty product reflective surface 276 is included on the carrier 202 and includes a beam opening to allow the emitted beam to pass through the beam aperture or opening and reflect off the empty product reflective surface. In general, however, the empty product reflective surface 276 may be located at any position on the dispensing unit 2 to reflect the empty product quantity sensor 272 beam. For example, the empty product quantity sensor 272 beam may be oriented in a similar manner as the low product quantity sensor described above so that the empty product reflective surface 276 is located behind the channel 10. Also similar to the preceding example, the empty product quantity sensor 272 may provide a signal indicating that the channel 10 is empty to the control unit 8. Also, it should be appreciated that any number of quantity detecting sensors may be utilized in the linear dispensing unit 2 to detect any quantity of products in a channel 10.

Figure 20:
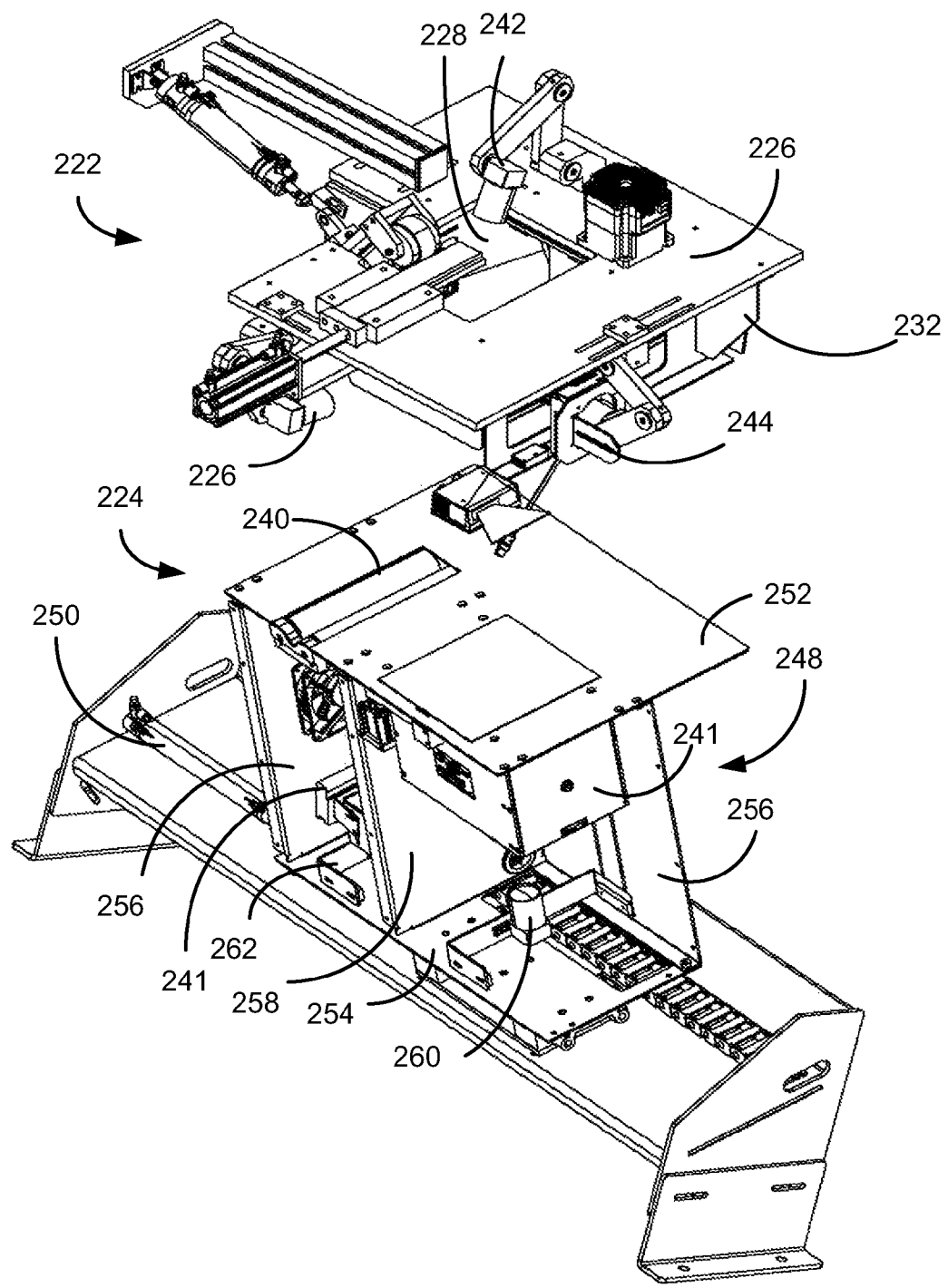
FIG. 20 is side perspective view of the escapement and light box shuttle assemblies of the alternate embodiment.
Figure 21:
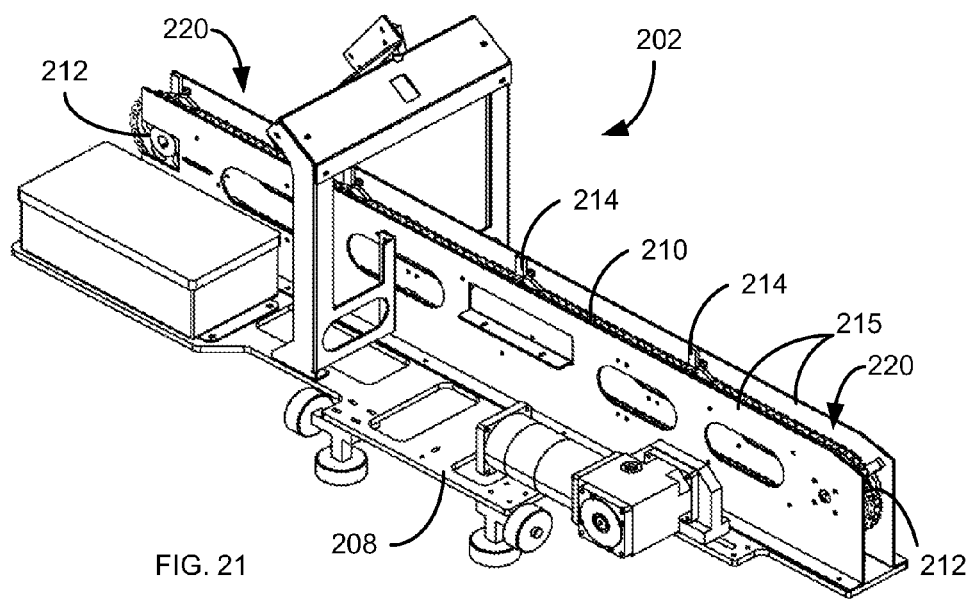
FIG. 21 is a side perspective view of the carrier of the alternate embodiment with parts broken away to show the drive chain assembly.
Figure 22:
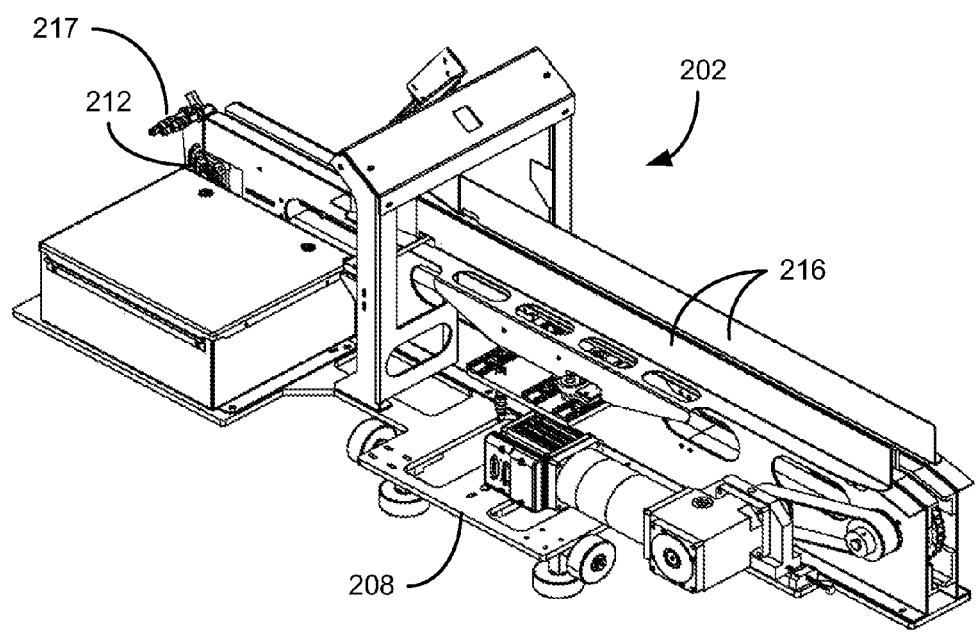
FIG. 22 is a side perspective view similar to that of FIG. 21 showing the carrier product guides.

Turning now to FIGS. 19 and 20, the universal discharge or escapement assembly 204 includes an escapement structure 222 and a light box shuttle assembly 224. The escapement structure 222 is connected to the exterior of the housing 20 of the linear dispensing unit 200 at a discharge aperture 56. In one embodiment, the escapement structure is configured to be freestanding and independent of the linear dispensing unit housing 200.

The escapement structure 222 receives the product package from the carrier 202 and also serves as a mounting platform for a plurality of imaging devices, such as optical readers, scanning devices, cameras or any combination thereof (FIGS. 19-20 & 29-36). The cameras are mounted at various locations on the structure 222 and are configured to obtain images of the product before and after the printed label is applied to the product package, as well as images of product information printed on the side and end portions of so-called "flats", that is, packages such as boxes or the like having generally flat surfaces. They are also configured to obtain images of product information printed on the end and side portions of so-called "rounds", that is packages such as bottles or the like having generally cylindrical sidewalls, and of product information printed on the sides and ends of irregularly shaped packages.

The light box shuttle assembly 224 may contain any number of imaging devices, such as optical readers, scanning devices, cameras or any combination thereof. For example, one camera may be mounted and configured to obtain images of product information printed on the bottom surfaces of flats, while another may be mounted and configured to obtain images of product information printed on the sidewalls of rounds and irregularly shaped packages. The product package information for both flats and rounds may include any useful information regarding the packaged product, the manufacturer, labeler, expiration date, and reference to any applicable product registry. For example, in the case of product packages containing a pharmaceutical intended for human use, the package is imprinted with the National Drug Code (NDC), lot and expiration numbers. In addition, any number of cameras may be associated with any number of lighting sources 241 to aid the cameras or imaging devices in detecting information on the product. For example, the light box may include a light or red light that illuminates the viewing aperture 228 to aid a camera 260 in reading the information on the product. In a similar manner, other cameras may also include a lighting source 241 to aid the camera in reading the information.

The escapement structure 222 (FIG. 20) includes a top wall 226, including an aperture 228, a bottom wall 230 and four sidewalls 232. A pair of product guides 234 depends from the top wall 226. The distance between the guides 234 may be adjusted to move them toward and away from each other as necessary to accommodate the width of the product(s) transferred from the carrier 202. Thus adjusted, the product guides 234 cooperate to form a guide chute to receive the product as it is ejected from the carrier 202.

A first camera 242, is mounted on the top wall 226 and positioned so that its lens may be aligned for imaging through the aperture 228, thereby avoiding interference from other elements of the escapement structure 222 (FIGS. 20, 29-36). Camera 242 is positioned in this manner so that it can obtain one or more clear images of each of the printed labels applied to a product package. A second camera 244 is mounted below the top wall 226 and positioned so that its lens may extend below the wall 226 for obtaining images of the side of flats within the structure 222. A third camera 246 is also mounted below the top 226 and positioned so that its lens may extend below the top for obtaining images of the ends of flat or round packages deposited within the structure 222. A fourth camera 260 is mounted below the product to obtain an image of the product through a window or aperture of the bottom wall 230. The second camera 244 is depicted as being positioned for obtaining images from a first side of the inventory package. It is foreseen that any number of additional cameras may be mounted for obtaining images of the opposite, second side of the inventory package. It is also foreseen that one or more of the cameras could be mounted on one or more sidewalls 232 of the escapement structure. The sidewalls 232 can be appropriately apertured to facilitate positioning of the camera lenses for imaging the product inside the structure.

The light box shuttle assembly 224, (FIGS. 20, 29-36) includes a housing 248 that rides on a cylinder 250 (FIG. 20), which enables it to move independently and to pass the assembly with its cameras back and forth beneath the escapement structure 222. The housing 248 includes a top wall 252, a bottom wall 254 and four sidewalls 256. The top wall 252 is constructed of a transparent material such as glass or synthetic resin. A product hold door 236 (FIGS. 29-36) is provided above the top wall 252 and is normally positioned transverse to the ends of the escapement product guides 234 to serve as a stop for the product as it reaches the end of the chute formed by the guides. A retractable product hold back tab 238 (FIGS. 29-31) is also provided. The hold back tab 238 may be raised above the surface of the top wall 252 to serve as an alternate stop for the product when the hold door 236 is moved out of position or away to allow camera access to the end of the product (FIG. 31). The light box shuttle assembly 224 also includes a pair of rollers 240, mounted on the top wall 252 for rotation about a longitudinal axis for receiving and rolling Round-type product packages.

An upstanding partition wall 258 divides the housing 248 into first and second side-by-side compartments as best shown in FIG. 20. The first compartment houses a fourth camera 260 that is positioned so that its lens extends upwardly for obtaining images of the bottom-facing sides of flat packages within the escapement structure 222. The second compartment houses a line scan camera 262, also positioned so that its lens extends upwardly for obtaining images of cylindrical products positioned within the escapement structure 222. Both the fourth camera and the line scan camera (260 and 262) capture images through the transparent housing top wall 252 or apertures therethrough.

A flap-fold label printer module 206 is illustrated in FIG. 19, although any other suitable label printer module may employed. The printer module 206 includes structure for printing "flap fold" type labels, that is to say label stock having on one side a printable surface, and on the reverse side an adhesive surface. After the printable surface has been printed, a portion of one of the free ends of the label is folded under on itself, so that the adhesive surfaces meet and the free end adheres to the inboard adhesive surface of the label. This forms a two layer flap having a printed surface on both sides. The remaining unfolded portion of the label has on one side a printed surface and on the reverse side an adhesive surface, which may be adhered to a product package. While the label may be folded at any point to form the flap, about two thirds of the label is customarily used to form the flap, leaving about one third of the label adhesive surface available for contacting and adhering to a product package. The flap fold label module 206 includes a labeler tamp pad 264.

In use, one or more carriers 202 are moved to desired locations along the linear track assembly 12 and the control unit 8 communicates with the carrier 202 to adjust the product guides 216 as previously described to form a channel that will accommodate the width of the selected products. The control unit 8 then commands rotation of the drive chain 210 in each carrier unit 202 about the sprockets 212 until the picker 214 pulls the inventory product from the channel and into one of the receiving zones 220 on the carrier unit 202. Each carrier has the capacity to pick up to three separate width compatible products. Once the carrier unit 202 is loaded, the control unit 8 commands the carrier to move to a discharge area as previously described. The discharge area may be selected without regard to the product shape, since a universal escapement assembly positioned at the discharge area is capable of receiving and labeling both flat sided and cylindrical (flats and rounds) or irregular shaped products. The control unit 8 commands movement of the drive chain to cause the pickers or dogs to discharge the product into the escapement structure 222. The control unit 8 also commands opening of the product guides 234 to the appropriate width to receive the product when it is discharged from the carrier 202. The ejected product slides through a chute formed by the product guides 234 until it encounters and is stopped by the product hold door 236.

Product information, such as the NDC, lot number and expiration date may be printed on the bottom, side or end of the manufacturer's product packaging, or unit of use packaging. On approximately seventy percent of product packages, this information is printed on the bottom surface of the package. The order profile for a particular client specifies the shape and size of the ordered package as well as the number of items. The control unit 8 uses data from the order profile to select the appropriate imaging camera unit to obtain images from the manufacturer's label for use in verification and labeling.

Where the manufacturer's product information is printed on the bottom of a flat sided package, the lens of the fourth camera 260, which is positioned in the light box shuttle housing 248 for upward aiming, captures the bar code information through the glass top 252 of the shuttle housing. The fourth camera is shuttled into position under the product by the light box shuttle assembly 224. The camera unit 260 transmits the scanned product information to the control unit 8, which uses software to verify that the correct product is in place.

By the time the product is in place and has been scanned, the control unit 8 has already transmitted the manufacturer's label content instructions to the labeler module 206. A label is printed in accordance with the control instructions, flap folded and held in place on the label tamp pad 264 by vacuum suction pending verification. In the event that the product information obtained by the fourth camera does not match the manufacturer' label information, or in the event that the fourth camera transmits information that no product is in place, then the controller instructs the label pad 266 to be extended toward the tamp pad 264 to receive the label. In this manner, the label is prevented from application to any product package in the event that verification cannot be obtained. If verification is obtained, the control unit 8 instructs the tamp pad 264 to apply the label to the product via software and machine control of the tamp pad.

After the tamp pad is withdrawn, the first camera 242, which is positioned for imaging the printed label, captures the information printed on the label and transmits this information to the control unit 8. The control unit 8 uses software to verify that the label matches the product. Once the information has been verified, the controller 8 instructs opening of the holdback door 236 (FIG. 32) and actuation of an air jet may be employed to eject the labeled product into a tote 19.

Figure 29:
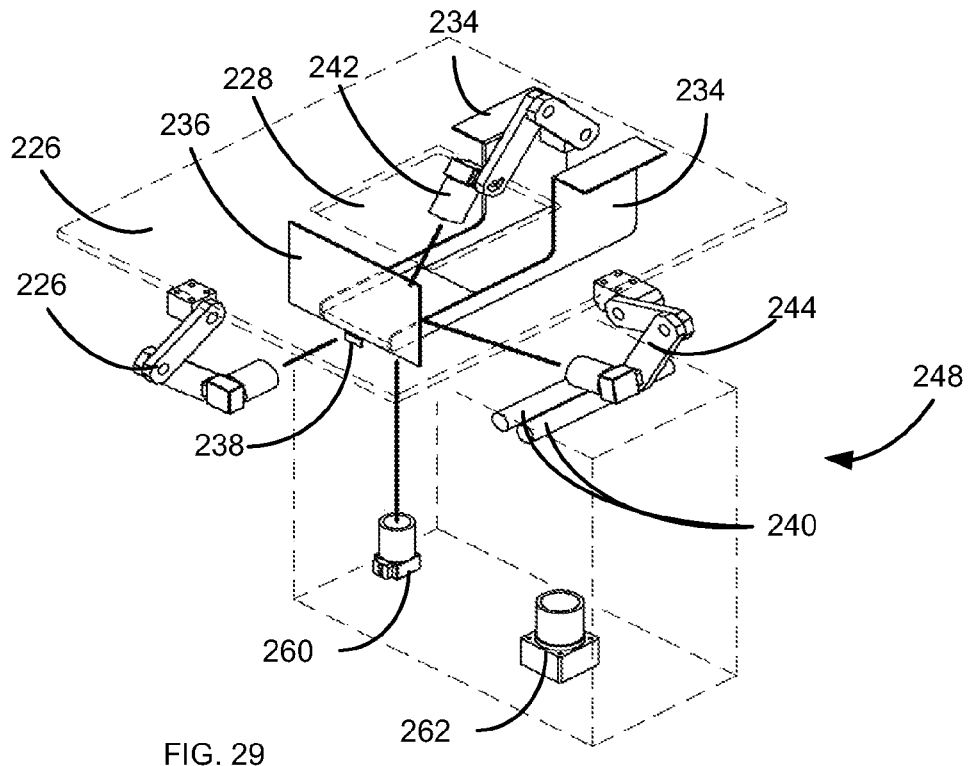
FIG. 29 is a perspective view of the escapement and light box shuttle assemblies of the alternate embodiment with a flat sided package in place and with parts omitted to show the cameras.
Figure 30:
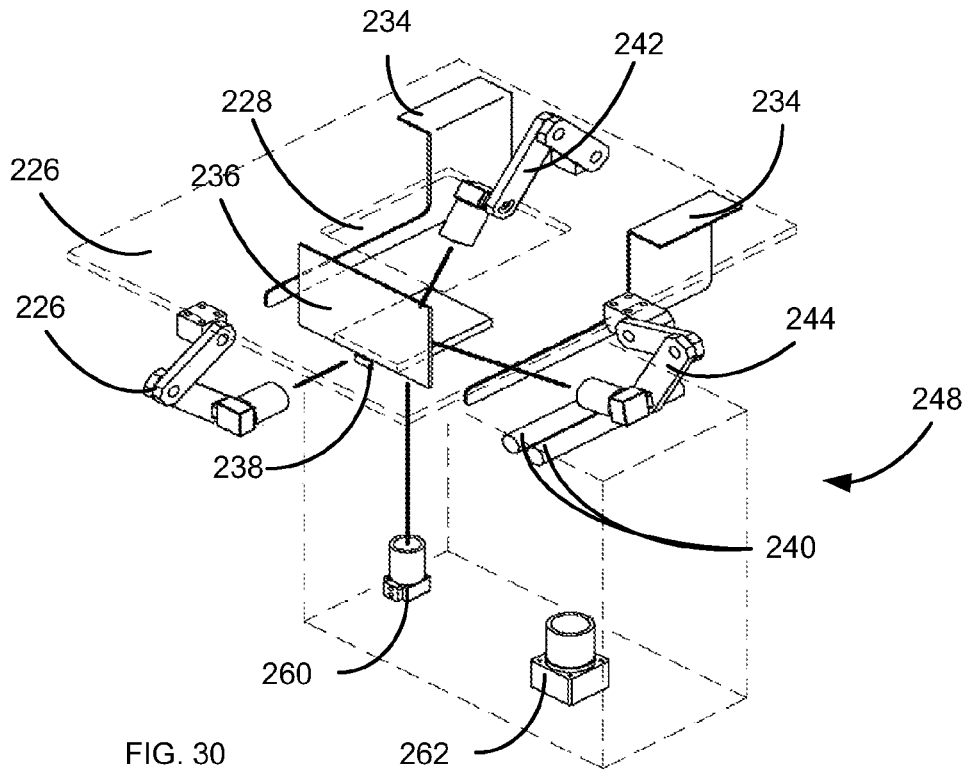
FIG. 30 is a perspective view similar to that of FIG. 29 showing the product guides in an open position for access by the second camera number.
Figure 31:
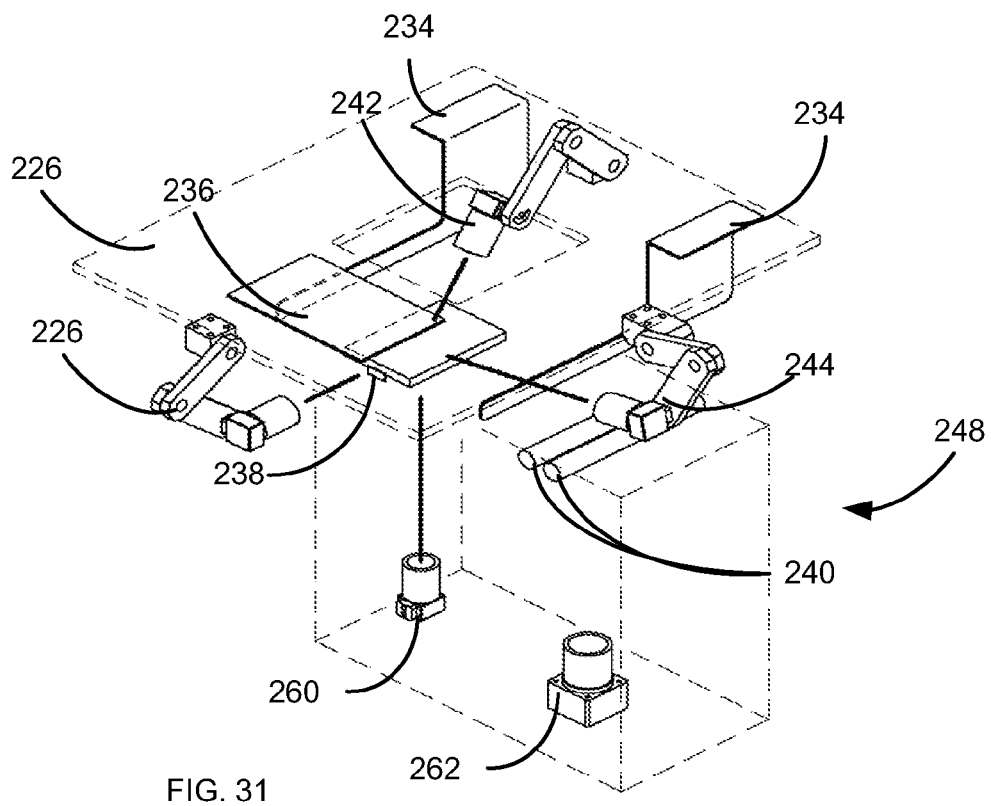
FIG. 31 is a perspective view similar to that of FIG. 30 showing the product hold door in an open position and the product hold back tab in an extended position for access by the third camera.

If the product information is printed on the side of the product package, the package is stopped at the hold door 236 as previously described and shown in FIG. 29, and the product guides 234 are moved to a fully open position as shown in FIG. 30. This position enables the second camera 244, which is positioned for obtaining an image of the side of the product, to obtain a clear view of the side of the product. It is also foreseen that the product guides 234 may be constructed of a transparent material such as glass or synthetic resin to enable them to remain in place without impairing the image obtained by the second camera.

Figure 32:
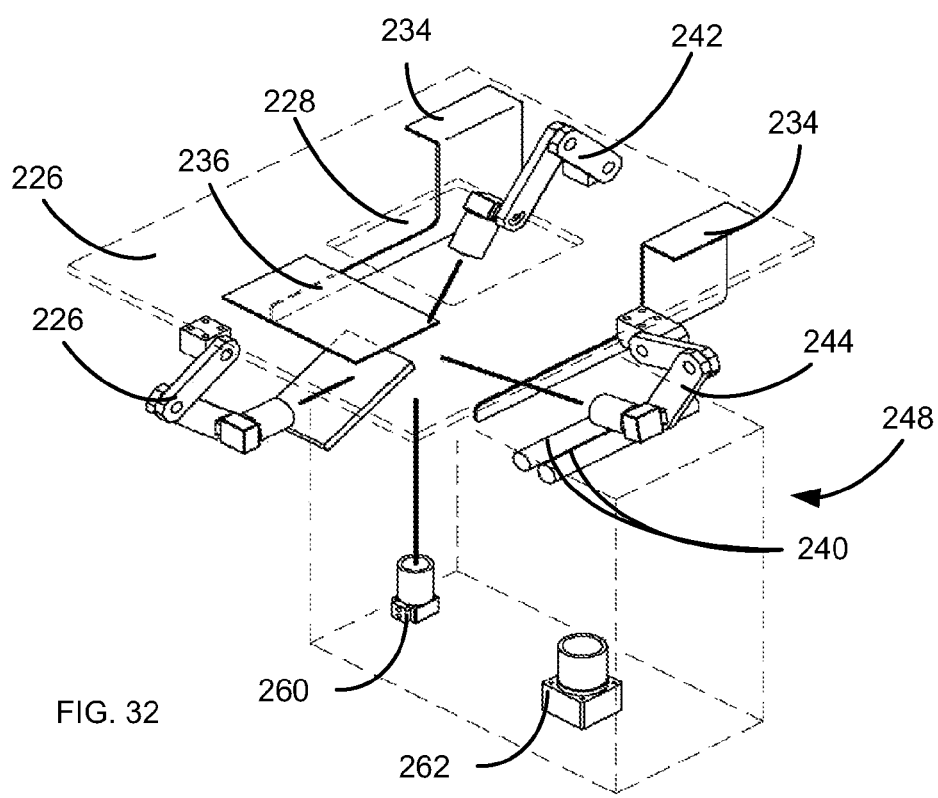
FIG. 32 is a perspective view similar to that of FIG. 31 showing the product hold back tab in a retracted position and a flat-sided product being ejected form the escapement.
Figure 33:
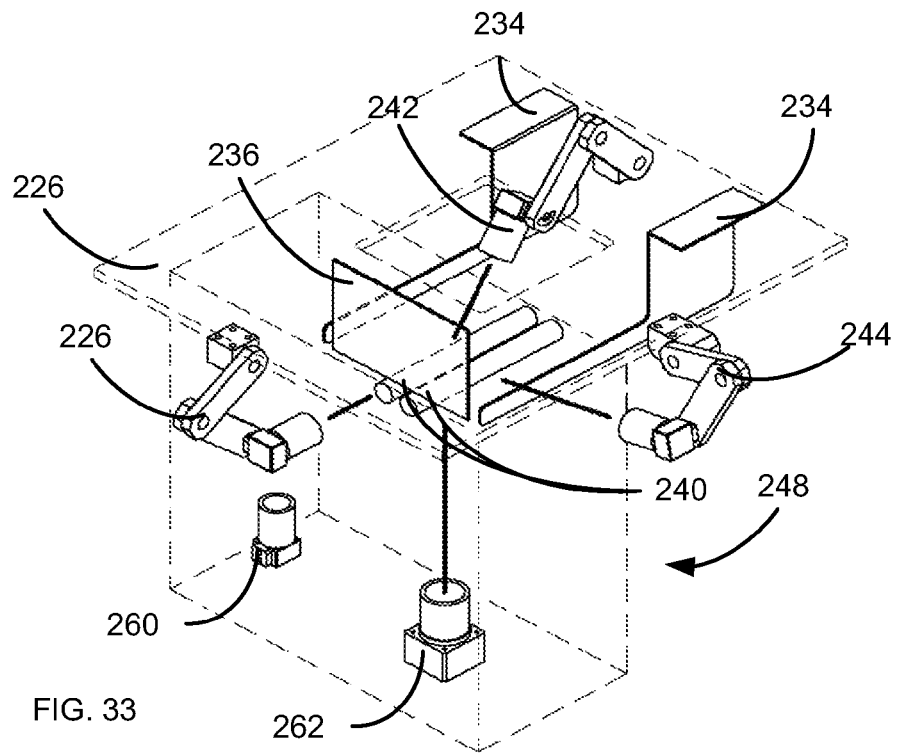
FIG. 33 is a perspective view of the escapement and light box shuttle assemblies of the alternate embodiment with the product guides and hold door repositioned adjacent the rollers.
Figure 34:
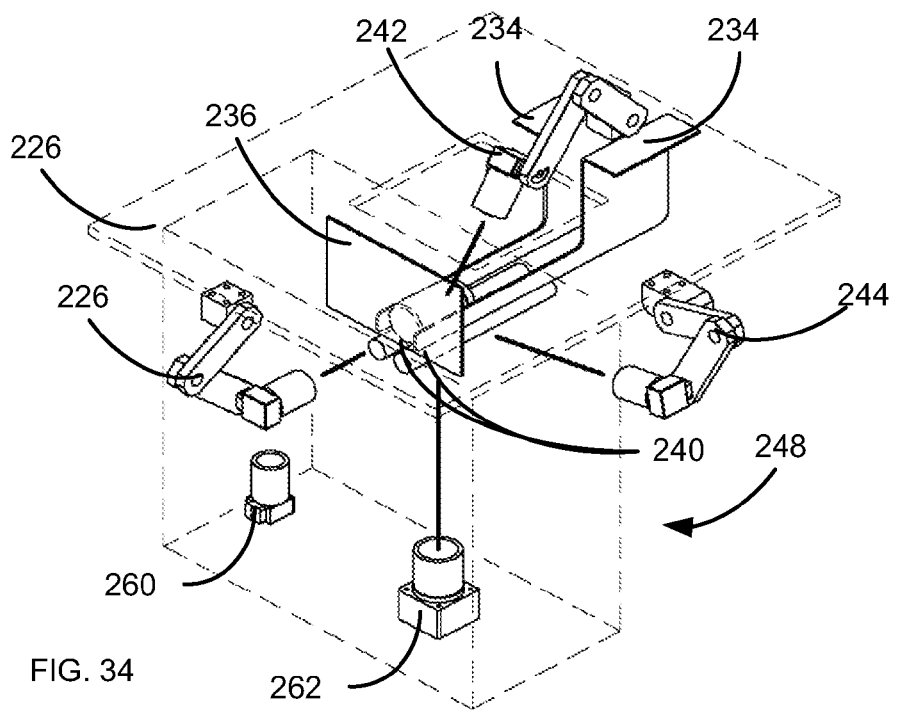
FIG. 34 is a perspective view similar to that shown in FIG. 33 with a round type product in place.
Figure 35:
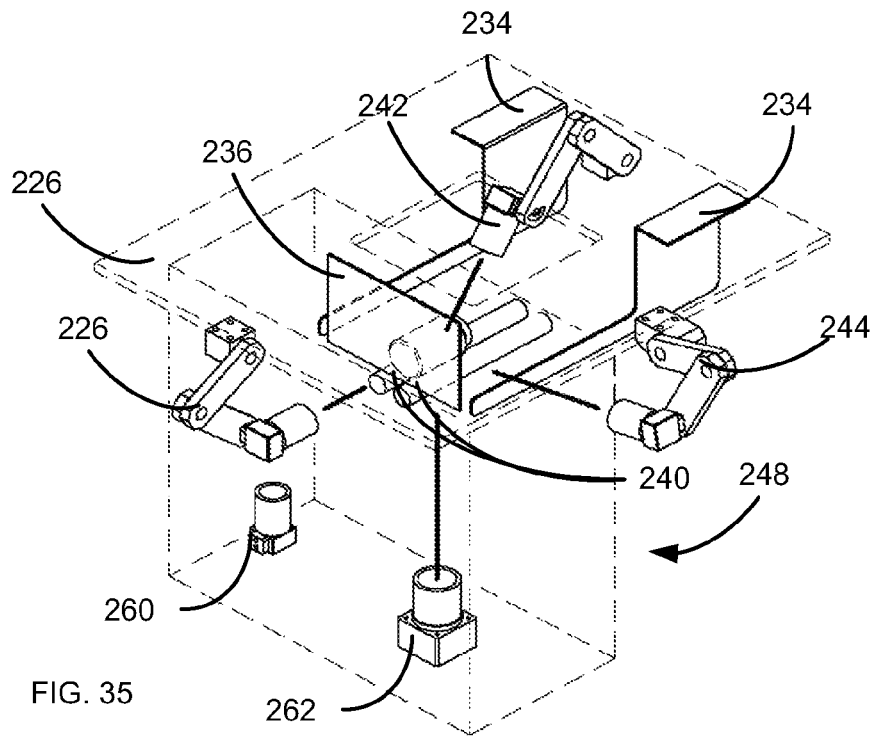
FIG. 35 is a perspective view similar to that shown in FIG. 34 with the product guides in an open position to enable imaging of the product bar code by the second camera.
Figure 36:
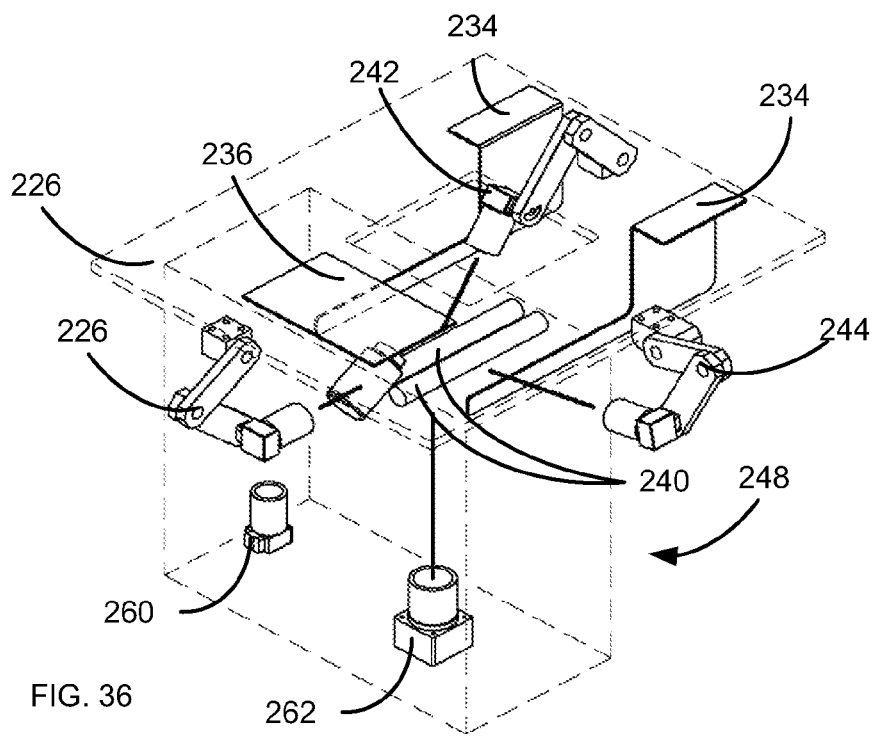
FIG. 36 is a perspective view similar to that shown in FIG. 35 showing the product hold door in a retracted position and the cylindrical product being ejected form the escapement.

If the product information is printed on the end of the product package, the product hold back tab 238 is extended to serve as a stop for the product rather than the product hold door 236 (FIG. 31). A pneumatic cylinder (not shown) is provided to actuate the hold back tab so that it pops up to extend above the surface of the top wall 252 of the light box shuttle housing 248. The tab 238 is preferably upstanding for a distance of about one eighth inch or less, so that it does not obscure any product package information. This enables the third camera 246, which is positioned for obtaining an image of the end of the product, to obtain an image of the product information. Once the labeling and verification process is complete, the control unit 8 instructs retraction of the hold back tab 238 to permit ejection of the labeled product into a tote 19 (FIG. 32). Alternatively, it is foreseen that the product hold door 236 may be constructed of a transparent material such as glass or a synthetic resin, to enable imaging therethrough.

Where the product package is generally cylindrical (a "round") or irregular in shape, the program control unit 8 selects the line scan camera 262. This camera, which is housed in the light box shuttle assembly 224, is shuttled into position under the product package as shown in FIG. 33. Cylindrical products or rounds are ejected from the carrier 202 onto a pair of rollers 240 that are positioned on the top wall 252 of the light box shuttle assembly. The product guides 234 are also repositioned on either side of the product rollers 240 (FIG. 34). The line scan camera is designed to capture linear images along the length of a cylindrical container or irregular package as the container or package is rotated about its longitudinal axis by the rollers 240. Computer software extracts the bar code from the image and constructs the bar code from the image and also identifies the location of the product package information on the package. Once the image is captured, the controller 8 instructs the rollers 240 to rotate the container or package so that the bar code with NDC, lot and expiration number is at a safe position, so that information such as the lot and expiration number are oriented so that the label will not be applied over the bar code. In another embodiment, a drive belt (not shown) may be pressed against the product opposite the rollers such that activation of the drive belt by the controller 8 causes the product to rotate. In this embodiment, the rollers may facilitate the rotation of the product by similarly rotating as the drive belt rotates the product. Once verification and labeling are complete, the controller 8 instructs the product guides 234 to retract (FIG. 35) to permit shifting of the product door 236 upwardly and out of the way, so that the product can be ejected by an air jet into a tote 19 (FIG. 36).

In this manner, the described multi-stage carrier 202 can select a plurality of products from various ones of the channels 10, deliver them to a universal escapement assembly 204 equipped with a light box shuttle assembly 224 where a flap-fold label is printed, applied and the label and product are verified, all without regard to whether the package shape is flat or round.

GENERAL INTERPRETATION OF TERMS

In understanding the scope of the present invention, the term "configured" as used herein to describe a unit, component, or part of a device includes hardware and/or software that is constructed and/or programmed to carry out the desired function. In understanding the scope of the present invention, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" or "element" when used in the singular can have the dual meaning of a single part or a plurality of parts. Finally, terms of degree such as "substantially", "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies.

What is claimed is:

1. A linear dispensing system comprising:
   a plurality of channels configured to hold inventory products of different types and shapes at an orientation;
   a linear track assembly including one or more linear motor modules, rails and one or more carriers slidably engaged at the rails, the linear motor module being disposed at the rails and having a linear synchronous motor to move the carrier, the carrier magnetically communicating with the linear motor module and having a conveyor unit configured to pick the inventory products from selected channels, the carrier conveyor unit including a guide mechanism having a first guide member and a second guide member movably disposed at an upper surface of the carrier conveyor unit to guide the inventory product along the conveyor unit in substantially the same orientation as in the channel;
   a labeler module configured to label the inventory products at substantially the same orientation; and,
   a discharge guide assembly for receiving the inventory products from the carriers and including a feeder portion and a support portion that cooperate to form a chute for directing the inventory product to the labeler module at substantially the same orientation.

2. The linear dispensing system of claim 1, further comprising a stabilizer mechanism disposed at the labeler module and including a movable stabilizer plate configured to selectively support the inventory product during labeling and to selectively release the inventory product.

3. The linear dispensing system of claim 1, wherein the first and second guide members are substantially parallel to one another.

4. The linear dispensing system of claim 1, wherein the guide mechanism further includes a guide actuator and first and second guide supports that link the first and second guide members, respectively, to the guide actuator.

5. The linear dispensing system of claim 4, wherein the guide actuator is configured to move each of the first and second guide members toward or away from its compliment.

6. The linear dispensing system of claim 4, further comprising a control unit connected to the guide actuator and configured to control the linear motor modules to position the carriers, wherein the control unit is further configured to command the guide actuator to move the first and second guide members according to a width of a selected channel.

7. The linear dispensing system of claim 1, wherein the labeler module includes a reader component configured to read informational indicia on the inventory product.

8. The linear dispensing system of claim 1, wherein the labeler module includes a reader component configured to scan and capture an image of the inventory product.

9. The linear dispensing system of claim 8, further comprising a control unit connected to the reader component and configured to control the linear motor modules to position the carriers, wherein the reader component transmits the captured image of the inventory product to the control unit.

10. The linear dispensing system of claim 9, wherein the control unit is further configured to obtain the information on the inventory product from the captured image and verify the information with original information in a database to ensure accuracy.

11. A linear dispensing system comprising:
a plurality of channels configured to hold inventory products of different types and shapes at an orientation;
a pair of parallel rails disposed at a bottom portion of the channels;
a plurality of carriers slidably disposed on the rails, the carriers having a conveyor unit configured to pick the inventory products from selected channels, the carrier conveyor units each including a guide mechanism having a first guide member and a second guide member movably disposed at an upper surface of the carrier conveyor unit to guide the inventory product along the conveyor unit in substantially the same orientation as in the channel;
a plurality of linear motor modules disposed between the parallel rails and aligned end to end, the linear motor modules being coupled with the carriers and configured to pass the carriers to an adjacent linear motor module; and,
a discharge guide assembly configured to receive the inventory products from the carriers and including a feeder portion and a support portion that cooperate to form a chute to direct the inventory products for labeling at substantially the same orientation.

12. The linear dispensing system of claim 11, further comprising a labeler module configured to label the inventory product at substantially the same orientation.

13. The linear dispensing system of claim 12, wherein the labeler module includes a stabilizer mechanism configured to maintain the inventory product in substantially the same orientation as received.

14. The linear dispensing system of claim 12, wherein the labeler module includes a reader component configured to read informational indicia on the inventory product.

15. The linear dispensing system of claim 12, wherein the labeler module includes a reader component configured to scan and capture an image of the inventory product.

16. The linear dispensing system of claim 15, further comprising a control unit connected to the reader component and configured to control the linear motor modules to position the carriers, wherein the reader component transmits the captured image of the inventory product to the control unit.

17. The linear dispensing system of claim 16, wherein the control unit is further configured to obtain the information on the inventory product from the captured image and verify the information with original information in a database to ensure accuracy.

18. The linear dispensing system of claim 15, wherein the discharge guide assembly includes a slide plate having a glass portion integrally disposed in the slide plate.

19. The linear dispensing system of claim 18, wherein the reader component is disposed at the glass portion.

20. The linear dispensing system of claim 12, further comprising a stabilizer mechanism disposed at the labeler module and including a movable stabilizer plate configured to selectively support the inventory product during labeling and to selectively release the inventory product.

21. The linear dispensing system of claim 11, wherein the first and second guide members are substantially parallel to one another.

22. The linear dispensing system of claim 11, wherein the guide mechanism further includes a guide actuator and first and second guide supports that link the first and second guide members, respectively, to the guide actuator.

23. The linear dispensing system of claim 22, wherein the guide actuator is configured to move each of the first and second guide members toward or away from its compliment.

24. The linear dispensing system of claim 22, further comprising a control unit connected to the guide actuator and configured to control the linear motor modules to position the carriers, wherein the control unit is further configured to command the guide actuator to move the first and second guide members according to a width of a selected channel.

25. A linear dispensing system comprising:
a plurality of channels configured to hold inventory products of different types and shapes at an orientation;
a linear track assembly including one or more linear motor modules, rails and one or more carriers slidably engaged at the rails, the linear motor module being disposed at the rails and having a linear synchronous motor to move the carrier, the carrier magnetically communicating with the linear motor module and having a drive chain configured to pick a plurality of inventory products of different shapes from the channels and substantially maintain each product in the same orientation as in the channel;
a labeler module configured to label the inventory products at substantially the same orientation;
a universal escapement assembly configured to receive the inventory products of different shapes from the carrier in substantially the same orientation;
the universal escapement assembly including a slide plate having a glass portion integrally disposed on the slide plate; and
a reader disposed behind the glass portion of the slide plate to read informational indicia on the inventory products and scan images of the inventory products before labeling.

26. The linear dispensing system of claim 25, wherein the escapement assembly further includes:
a plurality of imaging devices configured to read informational indicia on the sides and ends of the inventory products; and
an imaging device configured to read informational indicia on a label after it is applied to the inventory product.

27. The linear dispensing system of claim 26, wherein the escapement assembly further includes:
a shuttle assembly including a plurality of imaging devices configured to read information indicia on the bottom of the inventory products.

28. The linear dispensing system of claim 27, wherein the shuttle assembly includes a cylinder configured to position the shuttle assembly below the inventory product.

29. The escapement assembly of claim 27, wherein the shuttle assembly imaging devices include a line scan camera configured to scan informational indicia on a cylindrical surface of the inventory product as it is rotated within the escapement assembly.

30. The escapement assembly of claim 25, further including first and second guide members movably disposed for receiving inventory products of various sizes therebetween.

31. The escapement assembly of claim 30, further including a stop for preventing the inventory product from exiting the guide members.

32. The escapement assembly of claim 31, wherein the stop is shiftable from a stopping position to a withdrawn position.

33. A linear dispensing system comprising:
a plurality of channels configured to hold inventory products of different types and shapes at an orientation;
a pair of parallel rails disposed at a bottom portion of the channels;
a plurality of carriers slidably disposed on the rails, the carriers having a drive chain configured to pick a plurality of inventory products of different shapes from the channels and substantially maintain each product in the same orientations as in the channel;
a plurality of linear motor modules disposed between the parallel rails and aligned end to end, the linear motor modules being coupled with the carriers and configured to pass the carriers to an adjacent linear motor module;
a labeler module configured to label the inventory products of different shapes;
a universal escapement assembly configured to receive the inventory products of different shapes from the carrier in substantially the same orientation;
the universal escapement assembly including a slide plate having a glass portion integrally disposed on the side plate; and
a reader disposed behind the glass portion of the slide plate to read informational indicia on the inventory products and scan images of the inventory products before labeling.

34. The linear dispensing system of claim 33, wherein the escapement assembly further includes:
a plurality of imaging devices configured to read informational indicia on the sides and ends of the inventory products; and
an imaging device configured to read informational indicia on a label after it is applied to the inventory product.

35. The linear dispensing system of claim 33, wherein the escapement assembly further includes:
a shuttle assembly including a plurality of imaging devices configured to read information indicia on the bottom of the inventory products.

36. The linear dispensing system of claim 35, wherein the shuttle assembly includes a cylinder configured to position the shuttle assembly below the inventory product.

37. The escapement assembly of claim 35, wherein the shuttle assembly imaging devices include a line scan camera configured to scan informational indicia on a cylindrical surface of the inventory product as it is rotated within the escapement assembly.

* * * * *